United States Patent
Chen et al.

(10) Patent No.: US 9,994,579 B2
(45) Date of Patent: Jun. 12, 2018

(54) SALT OF PYRROLO[2,3-D]PYRIMIDINE COMPOUND AND NOVEL POLYMORPH OF SALT

(71) Applicant: Crystal Pharmatech Co., Ltd., Suzhou, Jiangsu (CN)

(72) Inventors: Minhua Chen, Jiangsu (CN); Yanfeng Zhang, Jiangsu (CN); Kai Liu, Jiangsu (CN); Jiaoyang Li, Jiangsu (CN); Xiaoyu Zhang, Jiangsu (CN)

(73) Assignee: Crystal Pharmatech Co., Ltd., Suzhou (CN)

(*) Notice: Subject to any disclaimer, the term of this patent is extended or adjusted under 35 U.S.C. 154(b) by 0 days. days.

(21) Appl. No.: 15/535,104

(22) PCT Filed: Dec. 11, 2015

(86) PCT No.: PCT/CN2015/097204
§ 371 (c)(1),
(2) Date: Jun. 12, 2017

(87) PCT Pub. No.: WO2016/091221
PCT Pub. Date: Jun. 16, 2016

(65) Prior Publication Data
US 2017/0342075 A1    Nov. 30, 2017

(30) Foreign Application Priority Data

Dec. 12, 2014  (CN) .......................... 2014 1 0768119
Dec. 18, 2014  (CN) .......................... 2014 1 0789045
Sep. 8, 2015   (CN) .......................... 2015 1 0566397

(51) Int. Cl.
| | |
|---|---|
| *C07D 487/04* | (2006.01) |
| *C07D 403/14* | (2006.01) |
| *C07D 401/14* | (2006.01) |
| *A61K 31/519* | (2006.01) |

(52) U.S. Cl.
CPC .......... *C07D 487/04* (2013.01); *A61K 31/519* (2013.01); *C07D 401/14* (2013.01); *C07D 403/14* (2013.01); *C07B 2200/13* (2013.01)

(58) Field of Classification Search
CPC .. C07D 487/04; C07D 401/14; C07D 403/14; A61K 31/519
USPC ........................................ 544/280; 514/265.1
See application file for complete search history.

(56) References Cited

FOREIGN PATENT DOCUMENTS

| CN | 102186856 | 9/2011 |
|---|---|---|
| CN | 103201275 | 7/2013 |
| CN | 105085533 | 11/2015 |
| CN | 105111215 | 12/2015 |
| CN | 105111215 A * | 12/2015 |

OTHER PUBLICATIONS

CN 105111215, 12-02-214;Google Search Machine Translation.*

* cited by examiner

*Primary Examiner* — Venkataraman Balasubramanian
(74) *Attorney, Agent, or Firm* — Fish & Richardson P.C.

(57) ABSTRACT

The present invention relates to novel crystalline forms of 7-cyclopentyl-2-(5-piperazin-1-yl-pyridin-2-ylamino)-7H-pyrrolo[2,3-d]pyrimidine-6-car boxylic acid dimethylamide (compound I), its salts, and process for preparation thereof. Crystalline forms in the present invention have good stability, low hygroscopicity, good processability, easy treatability and other favorable properties. In addition, the process is simple, low cost, and has an important value for future optimization and development of the drug.

(I)

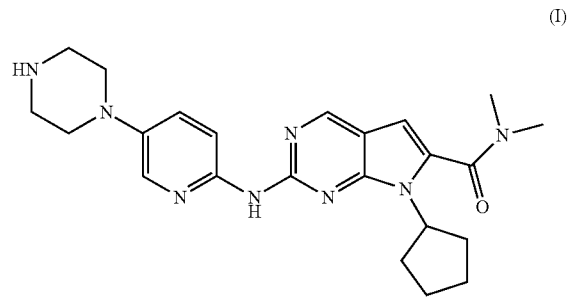

10 Claims, 18 Drawing Sheets

SALT OF PYRROLO[2,3-D]PYRIMIDINE COMPOUND AND NOVEL POLYMORPH OF SALT

TECHNICAL FIELD

The present invention relates to the field of pharmaceutical, especially salts of pyrrolo[2,3-d]pyrimidine and crystalline forms thereof.

BACKGROUND OF THE INVENTION

Cyclin-dependent kinase 4 and 6 (CDK4/6) are a group of serine/threonine kinases that drive cells through G1 into S phase by associating with cyclin D. The "cyclin D-CDK4/6-INK4-Rb pathway" is universally disrupted in human cancer and the alterations accelerating of G1 progression provides a survival advantage to cancer cells. Then, inhibition of CDK4 and CDK6 kinase activity may be a useful anticancer treatment.

LEE011 is a small molecule CDK4/6 inhibitor. It is developed by Novartis for the treatment of breast cancer and melanoma. The clinical form of LEE011 is succinate. LEE011 is currently in Phase III studies, and the Phase III shows positive data. The chemical name of LEE011 is 7-cyclopentyl-2-(5-piperazin-1-yl-pyridin-2-ylamino)-7H-pyrrolo[2,3-d]pyrimidine-6-carb oxylic acid dimethyl amide, and it has the structural of formula I:

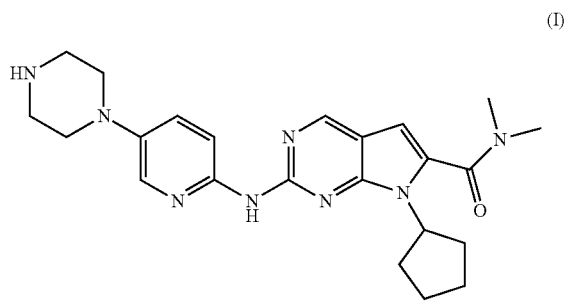 [SMILES: CN(C)C(=O)c1cc2cnc(Nc3ccc(N4CCNCC4)cn3)nc2n1C1CCCC1]

(I)

At present, CN103201275A reports a hydrate form and a non-hydrate form of compound I mono-succinate. The hydrate form has poor solubility, lower than 0.5 mg/mL in water. The non-hydrate form has better solubility. The inventor of the present invention discovered that the mono-succinate of the prior art is not stable and will have crystal transformation in high humidity, and it is not good enough for development and storage. At present, there is no other crystalline form of compound I and its salts.

Based on the situation, it is necessary to develop new crystalline forms which has good stability, low hygroscopicity, and is suitable for storage and industrial process. And the new forms should meet the requirements of further drug development.

SUMMARY OF THE INVENTION

The present invention provides salts of compound I, its crystalline forms and preparation process, which are suitable for pharmaceutical development and industrial process.

An objective of the present invention is to provide a hemi-succinate of compound I.

Further, the hemi-succinate provided by the present invention is in crystalline form, abbreviated as Form A.

Specifically, the X-ray powder diffraction pattern of the crystalline Form A shows characteristic peaks at 2theta values of 23.9°±0.2°, 20.0°±0.2°, 22.1°±0.2°.

Further, the X-ray powder diffraction pattern of the crystalline Form A shows one or two or three of the characteristic peaks at 2theta values of 22.0°±0.2°, 21.3°±0.2°, 13.0°±0.2°. Preferably, Form A shows characteristic peaks at 22.0°±0.2°, 21.3°±0.2°, 13.0°±0.2°.

Further, the X-ray powder diffraction pattern of the crystalline Form A shows one or two or three of the characteristic peaks at 2theta values of 4.7°±0.2°, 14.2°±0.2°, 10.6°±0.2°. Preferably, Form A shows characteristic peaks at 4.7°±0.2°, 14.2°±0.2°, 10.6°±0.2°.

Further, the X-ray powder diffraction pattern of the crystalline Form A of the present invention is substantially as shown in FIG. 1.

Another objective of the present invention is to provide a process for preparing crystalline Form A of hemi-succinate, which comprises: adding compound I and succinic acid or compound I mono-succinate in alcohols, ketones, ethers, esters or a mixture of alcohols or ketones or ethers or esters with water, stirring until solids precipitate out.

Further, said alcohol is ethanol, said ketone is acetone, said ester is ethyl acetate, said ether is tetrahydrofuran.

Compared with the prior art, firstly, hemi-succinate Form A is more physically stable, particularly it is stable at various humidity. Secondly, the mono-succinate prepared by prior art will easily have crystal transformation in various solvents, and has poor reproducibility in process development.

Another objective of present invention is to provide a pharmaceutical composition comprising a therapeutically effective amount of hemi-succinate Form A and pharmaceutical acceptable carrier. Generally the therapeutically effective amount of hemi-succinate Form A is mixed or contacted with one or more pharmaceutical excipients to prepare pharmaceutical composition or formulation. The pharmaceutical composition or formulation is prepared by well-known methods in pharmaceutical field.

The pharmaceutical composition of hemi-succinate Form A can be used for preparing drugs in the treatment of cancer, especially for preparing drugs in the treatment of breast cancer and melanoma.

Another objective of the present invention is to provide a new crystalline form of compound I mono-succinate, abbreviated as Form I, which has good stability, low hygroscopicity, and is suitable for storage and industrial process.

Particularly, the X-ray powder diffraction pattern of the crystalline Form I of the present invention shows characteristic peaks at 2theta values of 11.9°±0.2°, 19.4°±0.2°, 20.6°±0.2°.

Further, the X-ray powder diffraction pattern of the crystalline Form I shows one or two or three of the characteristic peaks at 2theta values of 22.7°±0.2°, 24.4°±0.2°, 26.3°±0.2°. Preferably, Form I of the present invention shows characteristic peaks at 22.7°±0.2°, 24.4°±0.2°, 26.3°±0.2°.

Further, the X-ray powder diffraction pattern of the crystalline Form I shows one or two or three of the characteristic peaks at 2theta values of 7.8°±0.2°, 15.7°±0.2°, 16.7°±0.2°. Preferably, Form I shows characteristic peaks at 7.8°±0.2°, 15.7°±0.2°, 16.7°±0.2°.

Further, the X-ray powder diffraction pattern of the crystalline Form I of the present invention is substantially as shown in FIG. 5.

Form I of mono-succinate of the present invention is an anhydrate. The differential scanning calorimetry analysis curve (DSC) of crystalline Form I shows an endothermic peak around 197° C. (onset temperature), which is substantially as shown in FIG. 7.

The thermal gravimetric analysis (TGA) thermogram of crystalline Form I of the present invention shows about 2.0% weight loss up to 178° C., which is substantially as shown in FIG. 8.

Another objective of present invention is to provide a process for preparing crystalline Form I of compound I mono-succinate, which comprises: dissolving compound I mono-succinate in a mixture of alcohols with one or more solvent selected from alkyl nitriles, alkanes, or dissolving compound I mono-succinate in a mixture of alkyl nitriles with water, stirring until solids precipitate out.

Preferably, said alcohols are methanol and ethanol, or combination thereof, said alkyl nitrile is acetonitrile, said alkane is n-heptane. Specifically, said mixture are acetonitrile and methanol, or ethanol and n-heptane, or acetonitrile and water.

Another objective of present invention is to provide a pharmaceutical composition comprising a therapeutically effective amount of mono-succinate Form I and pharmaceutical acceptable carrier. Generally the therapeutically effective amount of mono-succinate Form I is mixed or contacted with one or more pharmaceutical excipients to prepare pharmaceutical composition or formulation. The pharmaceutical composition or formulation is prepared by well-known methods in pharmaceutical field.

Further, the pharmaceutical composition of mono-succinate Form I can be used for preparing drugs in the treatment of cancer, especially for preparing drugs in the treatment of breast cancer and melanoma.

Compared with prior art, mono-succinate Form I of the present invention is more physically stable. Specifically, firstly, the mono-succinate prepared by prior art will convert to Form I of the present invention at various temperature in specific solvent system. Secondly, Form I of the present invention is stable at high humidity, while the mono-succinate prepared by prior art will have crystal transformation at high humidity.

The mono-succinate Form I of the present invention has low hygroscopicity and no particular drying condition is required in preparation. Thus it simplifies preparation and post treatment process, and suitable for industrial process. The mono-succinate Form I of the present invention does not need a special storage condition, thus it lowers the cost of the storage and quality control.

Another objective of present invention is to provide a pharmaceutical composition comprising a therapeutically effective amount of hemi-succinate Form A or mono-succinate Form I or combination thereof and pharmaceutical acceptable carrier. Generally the therapeutically effective amount of hemi-succinate Form A or mono-succinate Form I or combination thereof is mixed or contacted with one or more pharmaceutical excipients to prepare pharmaceutical composition or formulation. The pharmaceutical composition or formulation is prepared by well-known methods in pharmaceutical field.

Further, the pharmaceutical composition of hemi-succinate Form A or mono-succinate Form I or combination thereof can be used for preparing drugs in the treatment of cancer, especially for preparing drugs in the treatment of breast cancer and melanoma.

Another objective of the present invention is to provide salts of compound I, comprising adipate, maleate and glycollate.

Further, the adipate of compound I of the present invention is in crystalline form, abbreviated as adipate Form A.

Specifically, the X-ray powder diffraction pattern of the adipate Form A of the present invention shows characteristic peaks at 2theta values of 22.2°±0.2°, 19.2°±0.2°.

Further, the X-ray powder diffraction pattern of the adipate Form A shows characteristic peaks at 2theta values of 24.9°±0.2°, 14.0°±0.2°, 16.1°±0.2°.

Further, the X-ray powder diffraction pattern of the adipate Form A shows one or two or three of the characteristic peaks at 2theta values of 18.0°±0.2°, 19.8°±0.2°, 4.8°±0.2°. Preferably, adipate Form A shows characteristic peaks at 18.0°±0.2°, 19.8°±0.2°, 4.8°±0.2°.

Further, the X-ray powder diffraction pattern of the adipate Form A is substantially as shown in FIG. 13.

The differential scanning calorimetry analysis curve (DSC) of adipate Form A of the present invention shows an endothermic peak around 177° C. (onset temperature), which is substantially as shown in FIG. 14.

The thermal gravimetric analysis (TGA) thermogram of adipate Form A of the present invention shows about 2.1% weight loss up to 159° C., which is substantially as shown in FIG. 15.

Further, the maleate of compound I of the present invention is in crystalline form, abbreviated as maleate Form A.

Specifically, the X-ray powder diffraction pattern of the maleate Form A of the present invention shows characteristic peaks at 2theta values of 18.6°±0.2°, 19.9°±0.2°, 14.9°±0.2°.

Further, the X-ray powder diffraction pattern of the maleate Form A shows one or two or three of the characteristic peaks at 2theta values of 24.5°±0.2°, 17.1°±0.2°, 16.5°±0.2°. Preferably, maleate Form A of this invention shows characteristic peaks at 24.5°±0.2°, 17.1°±0.2°, 16.5°±0.2°.

Further, the X-ray powder diffraction pattern of the maleate Form A shows one or two or three of the characteristic peaks at 2theta values of 21.9°±0.2°, 29.3°±0.2°, 8.5°±0.2°. Preferably, maleate Form A of this invention shows characteristic peaks at 21.9°±0.2°, 29.3°±0.2°, 8.5°±0.2°.

Further, the X-ray powder diffraction pattern of the maleate Form A of the present invention is substantially as shown in FIG. 16.

The differential scanning calorimetry analysis curve (DSC) of maleate Form A of the present invention shows an endothermic peak around 207° C. (onset temperature), which is substantially as shown in FIG. 17.

The thermal gravimetric analysis (TGA) thermogram of maleate Form A of the present invention shows about 3.1% weight loss up to 138° C., which is substantially as shown in FIG. 18.

Further, the glycollate of compound I of the present invention is in crystalline form, abbreviated as glycollate Form A.

Specifically, the X-ray powder diffraction pattern of the glycollate Form A of the present invention shows characteristic peaks at 2theta values of 21.3°±0.2°, 19.5°±0.2°, 23.3°±0.2°.

Further, the X-ray powder diffraction pattern of the glycollate Form A shows one or two or three of the characteristic peaks at 2theta values of 21.8°±0.2°, 12.4°±0.2°, 10.1°±0.2°. Preferably, glycollate Form A of this invention shows characteristic peaks at 21.8°±0.2°, 12.4°±0.2°, 10.1°±0.2°.

Further, the X-ray powder diffraction pattern of the glycollate Form A shows one or two or three of the characteristic peaks at 2theta values of 13.3°±0.2°, 16.8°±0.2°, 23.9°±0.2°. Preferably, glycollate Form A of this invention shows characteristic peaks at 13.3°±0.2°, 16.8°±0.2°, 23.9°±0.2°.

Further, the X-ray powder diffraction pattern of the glycollate Form A of the present invention is substantially as shown in FIG. 19.

The differential scanning calorimetry analysis curve (DSC) of glycollate Form A of the present invention shows an endothermic peak at 253° C. (onset temperature), which is substantially as shown in FIG. 20.

The thermal gravimetric analysis (TGA) of glycollate Form A of the present invention shows about 3.5% weight loss up to 176° C., which is substantially as shown in FIG. 21.

Another objective of the present invention is to provide a process for preparing adipate Form A, comprising: adding compound I and adipic acid in alcohols, ketones, or a mixture of alcohols or ketones with water, stirring until solids precipitate out.

Further, said alcohol is ethanol, said ketone is acetone.

Further, the volume ratio of said mixture of alcohols or ketones with water is 10:1 to 20:1.

Further, the mole ratio of compound I and adipic acid is 1:1~1:1.2.

Another objective of the present invention is to provide a process for preparing maleate Form A, which comprises: adding compound I and maleic acid in a mixture of ketones with water, stirring until solids precipitate.

Further, said ketone is acetone.

Further, the volume ratio of said ketone and water is 10:1 to 20:1.

Further, the volume ratio of said ketone and water is 19:1.

Further, the mole ratio of compound I and maleic acid is 1:0.9~1:1.2.

Another objective of the present invention is to provide a process for preparing glycollate Form A, comprising: adding compound I and glycolic acid in ketones, ethers or a mixture of ketones or ethers with water, stirring until solids precipitate out.

Further, said ketone is acetone, said ether is tetrahydrofuran.

Further, the volume ratio of said mixture of ketones or esters with water is 10:1 to 20:1.

Further, the mole ratio of compound I and glycolic acid is 1:1~1:4.5.

The crystalline adipate, maleate, glycollate of the present invention has low hygroscopicity and no particular drying condition is required in preparation, thus it simplifies preparation and post treatment process, and is suitable for industrial process. The water content of these three crystalline salts remain constant and does not need a special storage condition, thus it lowers the cost of storage and quality control. Compared with the mono-succinate non-hydrate form in CN103201275A, these three crystalline salts of the present invention are more stable. They will not easily have crystal transformation during storage, thus have great economic value.

Another objective of present invention is to provide a pharmaceutical composition comprising a therapeutically effective amount of crystalline adipate, maleate, glycollate of the present invention and pharmaceutical acceptable carrier. Generally the therapeutically effective amount of crystalline adipate, maleate, glycollate is mixed or contacted with one or more pharmaceutical excipients to prepare pharmaceutical composition or formulation. The pharmaceutical composition or formulation is prepared by well-known methods in pharmaceutical field.

Further, the pharmaceutical composition of crystalline adipate, maleate, glycollate of the present invention can be used for preparing drugs in the treatment of cancer, especially for preparing drugs in the treatment of breast cancer and melanoma.

DETAILED DESCRIPTION OF THE INVENTION

The present invention will be further explained by the specific embodiments, but are not intended to limit the scope of the present invention. The skilled in the art can make improvements to the process and the used instruments within the scope of the claims, and those improvements should be considered as falling into the scope of the present invention. Accordingly, the protective scope of the present invention patent should be defined by the appended claims.

The abbreviations used in the invention are explained as follows:

XRPD: X-ray Powder Diffraction
DSC: Differential Scanning calorimetry
TGA: Thermal Gravimetric Analysis
DVS: Dynamic Vapor Sorption
$^1$H NMR: $^1$H Nuclear Magnetic Resonance X-ray powder diffraction pattern in the present invention was acquired by a Panalytical Empyrean X-ray powder diffractometer. The parameters of the X-ray powder diffraction method of the present invention were as follows:

X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree The pattern of differential scanning calorimetry (DSC) in the present invention was acquired by a TA Q2000. The parameters of the differential scanning calorimetry (DSC) method of the present invention were as follow:

Heating rate: 10° C./min
Purge gas: nitrogen.

The pattern of thermal gravimetric analysis (TGA) in the present invention was acquired by a TA Q5000. The parameters of the thermal gravimetric analysis (TGA) method of the present invention were as follow:

Heating rate: 10° C./min;
Purge gas: nitrogen.

Dynamic Vapor Sorption (DVS) was measured via a SMS (Surface Measurement Systems) DVS Intrinsic. Typical Parameters for DVS test are listed below.

Temperature: 25° C.
Gas and flow rate: N2, 200 mL/min
dm/dt: 0.002%/min
RH range: 0% RH to 95% RH

EXAMPLE 1

Figure 1:
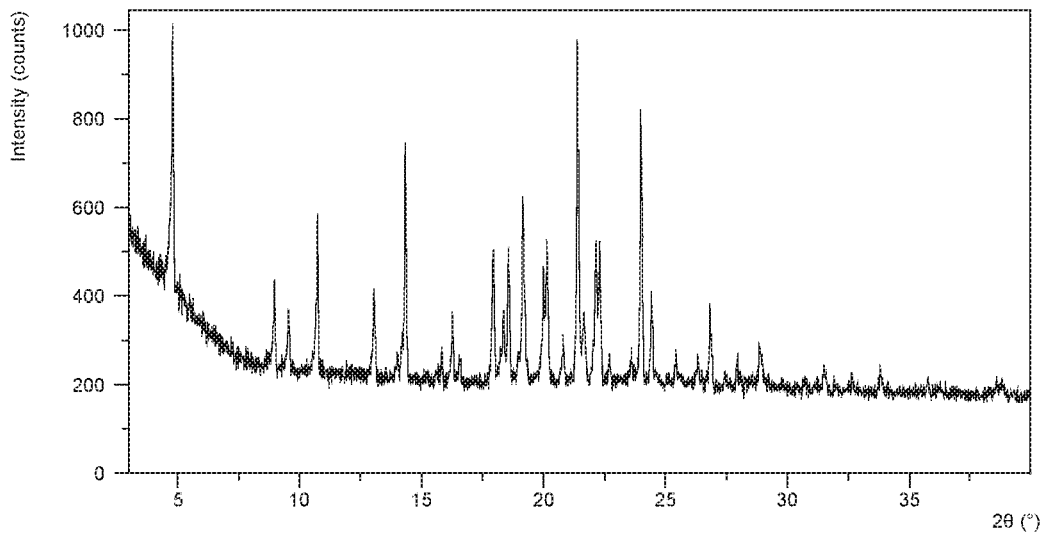
FIG. 1 XRPD pattern of hemi-succinate Form A.
Figure 2:
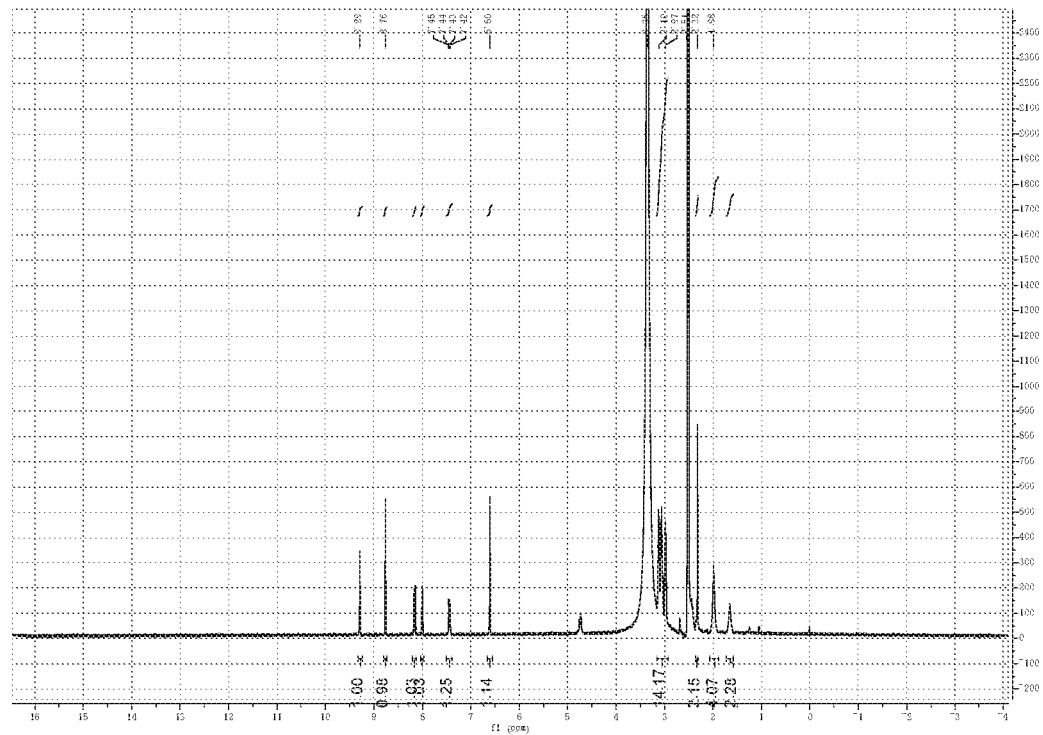
FIG. 2 $^1$H NMR spectrum of hemi-succinate Form A.

Process for Preparing Hemi-Succinate Form A:

10.5 mg of compound I freebase was added into ethanol, and 3.0 mg of succinic acid was added, then stirred at room temperature for 12 hours until solids precipitate out. Hemi-succinate Form A was analyzed by XRPD, DSC, TGA and $^1$H NMR. The XRPD data of the hemi-succinate Form A produced in this example is listed in Table 1. The DSC data shows an endothermic peak at 180° C. (onset temperature). The TGA data shows 12.5% weight loss up to 118° C. The XRPD pattern is displayed in FIG. 1, the $^1$H NMR spectrum is displayed in FIG. 2.

$^1$H NMR data of hemi-succinate Form A produced in this example is shown as following: $^1$H NMR (400 MHz, DMSO) δ 9.29 (s, 1H), 8.76 (s, 1H), 8.16 (d, J=9.0 Hz, 1H), 8.00 (d, J=2.9 Hz, 1H), 7.44 (dd, J=9.2, 3.0 Hz, 1H), 6.60 (s, 1H), 3.15-2.93 (m, 14H), 2.32 (s, 2H), 1.98 (s, 4H), 1.65 (s, 2H).

TABLE 1

| 2theta | d spacing | Intensity % |
|---|---|---|
| 4.69 | 18.84 | 71.02 |
| 8.87 | 9.97 | 23.85 |
| 9.45 | 9.36 | 16.73 |
| 10.64 | 8.32 | 41.57 |
| 12.96 | 6.83 | 23.59 |
| 14.24 | 6.22 | 63.46 |
| 15.73 | 5.63 | 7.33 |
| 16.17 | 5.48 | 18.29 |
| 16.47 | 5.38 | 6.10 |
| 17.83 | 4.97 | 34.08 |
| 18.26 | 4.86 | 20.26 |
| 18.47 | 4.80 | 37.64 |
| 19.04 | 4.66 | 51.36 |
| 19.89 | 4.46 | 34.73 |
| 20.04 | 4.43 | 40.63 |
| 20.70 | 4.29 | 11.44 |
| 21.29 | 4.17 | 100.00 |
| 21.57 | 4.12 | 17.28 |
| 22.04 | 4.03 | 40.12 |
| 22.20 | 4.00 | 40.13 |
| 22.61 | 3.93 | 7.68 |
| 23.88 | 3.73 | 78.70 |
| 24.32 | 3.66 | 25.92 |
| 25.33 | 3.52 | 7.29 |
| 26.20 | 3.40 | 6.47 |
| 26.72 | 3.34 | 24.03 |
| 27.83 | 3.21 | 7.19 |
| 28.78 | 3.10 | 11.72 |
| 31.42 | 2.85 | 5.46 |
| 32.50 | 2.76 | 2.50 |
| 33.72 | 2.66 | 5.12 |
| 38.65 | 2.33 | 2.58 |

EXAMPLE 2

Process for Preparing of Hemi-Succinate Form A:

10.2 mg of compound I freebase was added into tetrahydrofuran, and 2.8 mg of succinic acid was added, then stirred at room temperature for 12 hours until solids precipitate out. The XRPD data of the hemi-succinate Form A produced in this example is listed in Table 2.

TABLE 2

| 2theta | d spacing | Intensity % |
|---|---|---|
| 4.70 | 18.81 | 100.00 |
| 6.14 | 14.40 | 13.17 |
| 8.87 | 9.96 | 12.08 |
| 10.65 | 8.31 | 24.56 |
| 12.32 | 7.18 | 7.43 |
| 12.97 | 6.82 | 23.94 |
| 14.28 | 6.20 | 67.09 |
| 16.18 | 5.48 | 21.53 |
| 17.87 | 4.96 | 34.36 |
| 18.49 | 4.80 | 56.14 |

TABLE 2-continued

| 2theta | d spacing | Intensity % |
|---|---|---|
| 19.10 | 4.65 | 60.98 |
| 20.08 | 4.42 | 49.94 |
| 20.72 | 4.29 | 19.08 |
| 21.32 | 4.17 | 60.86 |
| 21.56 | 4.12 | 28.62 |
| 22.04 | 4.03 | 54.18 |
| 22.21 | 4.00 | 43.36 |
| 22.64 | 3.93 | 11.04 |
| 23.49 | 3.79 | 16.24 |
| 23.89 | 3.72 | 87.76 |
| 24.36 | 3.65 | 31.70 |
| 25.31 | 3.52 | 16.68 |
| 26.24 | 3.40 | 13.04 |
| 26.75 | 3.33 | 33.25 |
| 27.87 | 3.20 | 16.12 |
| 28.82 | 3.10 | 14.01 |
| 30.60 | 2.92 | 5.00 |
| 31.43 | 2.85 | 12.77 |
| 32.60 | 2.75 | 5.05 |
| 33.72 | 2.66 | 7.39 |
| 35.71 | 2.51 | 5.65 |
| 38.62 | 2.33 | 4.11 |

EXAMPLE 3

Figure 3:
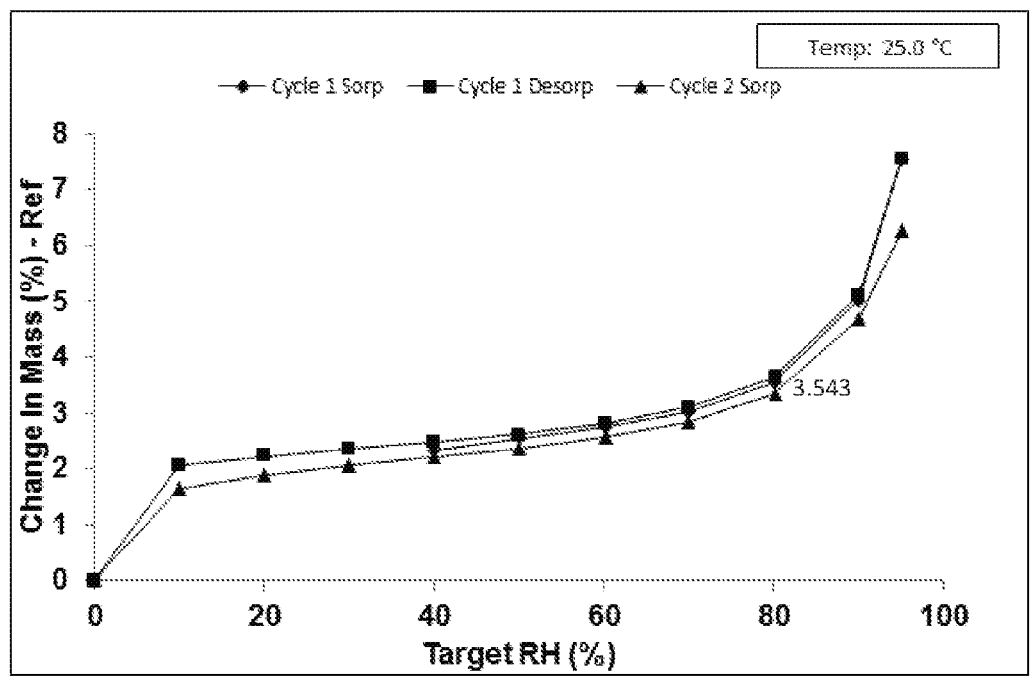
FIG. 3 DVS curve of hemi-succinate Form A.
Figure 4:
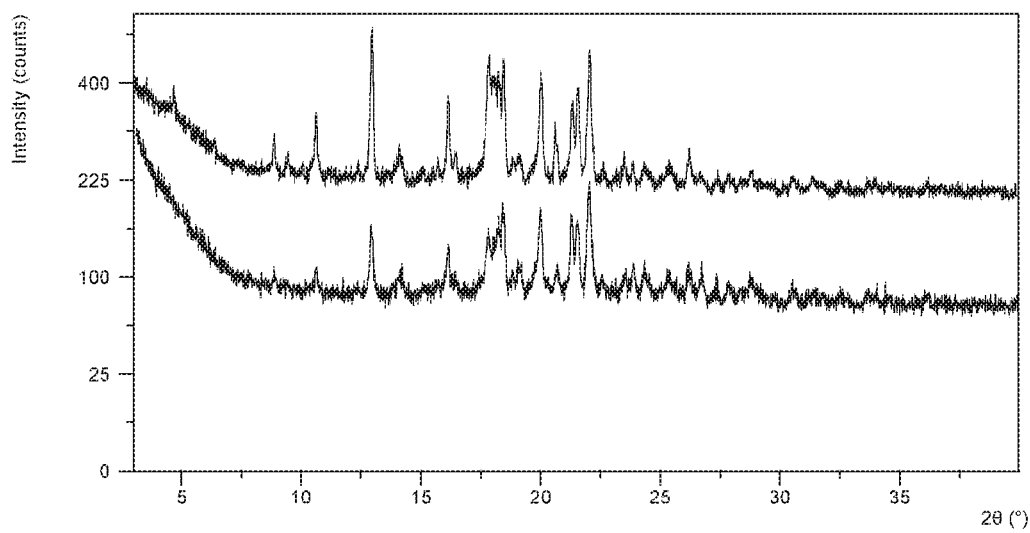
FIG. 4 XRPD overlay of hemi-succinate Form A before and after DVS (the pattern above is XRPD pattern of Form A before test, the pattern below is XRPD pattern of Form A after test)

Stability of Hemi-Succinate Form A at High Humidity:

About 10.0 mg of hemi-succinate Form A was analyzed by DVS. The solid form was tested by XRPD before and after DVS. The result showed that it has a 3.5% weight gain at 80% RH, which is slightly hygroscopic. The DVS curve was displayed in FIG. 3, the XRPD overlay pattern is displayed in FIG. 4.

About hygroscopicity characterization description and definition of hygroscopicity (Chinese Pharmacopoeia 2010 edition appendix XIXJ Drug hygroscopic test guidelines, test at 25° C.+/−1° C., 80% Relative Humidity)

- deliquescent: sufficient water is absorbed to form a liquid;
- very hygroscopic: increase in mass is equal to or greater than 15 percent;
- hygroscopic: increase in mass is less than 15 percent and equal to or greater than 2 percent;
- slightly hygroscopic: increase in mass is less than 2 percent and equal to or greater than 0.2 percent.
- no or almost no hygroscopic: increase in mass is less than 0.2%

EXAMPLE 4

Conversion Relationship Between Hemi-Succinate Form A and Mono-Succinate Non-Hydrate Form in Patent CN103201275A:

About 10 mg of the non-hydrate form in patent CN103201275A as starting form was added in different solvents or mixed solvents (v/v), then stirred at 5-50° C. for about 48 hours. Finally, the starting form converted to hemi-succinate Form A. Solvents used in this example is shown in table 3.

TABLE 3

| NO. | Starting Form | Solvent/Mixed solvent (v/v) | Final Form |
|---|---|---|---|
| 1 | mono-succinate in patent CN103201275A | Ethyl acetate | hemi-succinate Form A |
| 2 | mono-succinate in patent CN103201275A | Ethanol:water = 20:1 | hemi-succinate Form A |
| 3 | mono-succinate in patent CN103201275A | Acetone:water = 20:1 | hemi-succinate Form A |
| 4 | mono-succinate in patent CN103201275A | Tetrahydrofuran:water = 20:1 | hemi-succinate Form A |

EXAMPLE 5

Process for Preparing Mono-Succinate Form I:

30.7 mg of the non-hydrate form (prepared according to patent CN103201275A) was added into 2.2 mL of acetonitrile/methanol (v/v=10/1), then stirred at 50° C. for 48 hours, until solids precipitate out.

Figure 5:
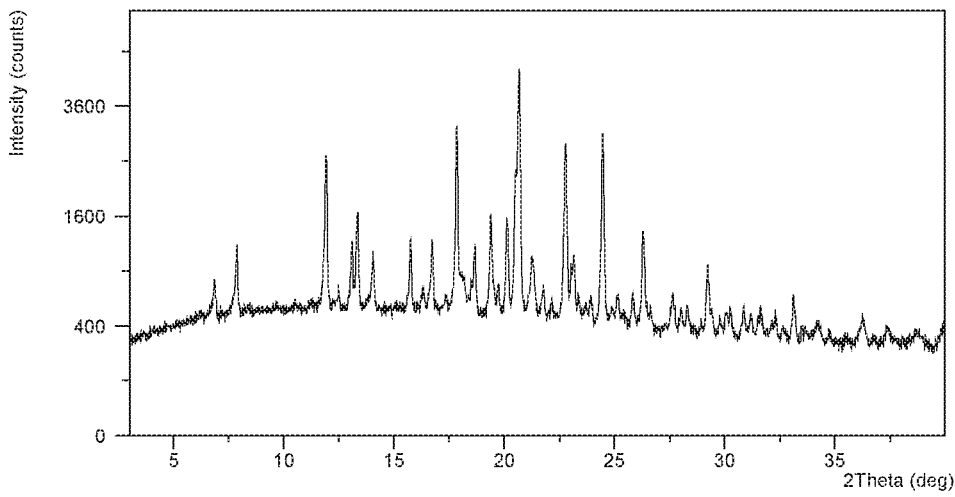
FIG. 5 XRPD pattern of mono-succinate Form I.

The XRPD data of the mono-succinate Form I produced in this example is listed in Table 4 and the XRPD pattern was displayed in FIG. 5.

TABLE 4

| 2theta | d spacing | Intensity % |
|---|---|---|
| 6.83 | 12.95 | 7.85 |
| 7.82 | 11.30 | 16.06 |
| 11.24 | 7.88 | 3.49 |
| 11.88 | 7.45 | 53.46 |
| 12.46 | 7.11 | 5.71 |
| 13.06 | 6.78 | 19.20 |
| 13.31 | 6.65 | 31.18 |
| 14.01 | 6.32 | 16.85 |
| 15.71 | 5.64 | 20.66 |
| 16.29 | 5.44 | 6.07 |
| 16.70 | 5.31 | 21.23 |
| 17.81 | 4.98 | 71.41 |
| 18.63 | 4.76 | 18.63 |
| 19.35 | 4.59 | 31.47 |
| 19.69 | 4.51 | 8.47 |
| 20.10 | 4.42 | 32.20 |
| 20.47 | 4.34 | 43.73 |
| 20.64 | 4.30 | 100.00 |
| 21.23 | 4.19 | 16.26 |
| 21.72 | 4.09 | 6.12 |
| 22.74 | 3.91 | 61.23 |
| 23.12 | 3.85 | 15.91 |
| 23.34 | 3.81 | 6.29 |
| 23.89 | 3.73 | 5.74 |
| 24.43 | 3.64 | 66.75 |
| 25.11 | 3.55 | 4.94 |
| 25.80 | 3.45 | 7.99 |
| 26.27 | 3.39 | 23.61 |
| 27.61 | 3.23 | 8.03 |
| 27.99 | 3.19 | 4.23 |
| 28.44 | 3.14 | 82.46 |
| 28.52 | 3.14 | 46.44 |
| 29.18 | 3.06 | 14.13 |
| 29.74 | 3.00 | 3.00 |
| 30.04 | 2.97 | 3.93 |
| 30.82 | 2.90 | 3.98 |
| 31.16 | 2.87 | 3.74 |
| 31.59 | 2.83 | 4.01 |
| 32.27 | 2.77 | 3.61 |
| 33.08 | 2.71 | 7.40 |
| 34.21 | 2.62 | 2.30 |
| 36.23 | 2.48 | 3.61 |
| 37.35 | 2.41 | 1.65 |
| 38.69 | 2.33 | 1.28 |

Figure 6:
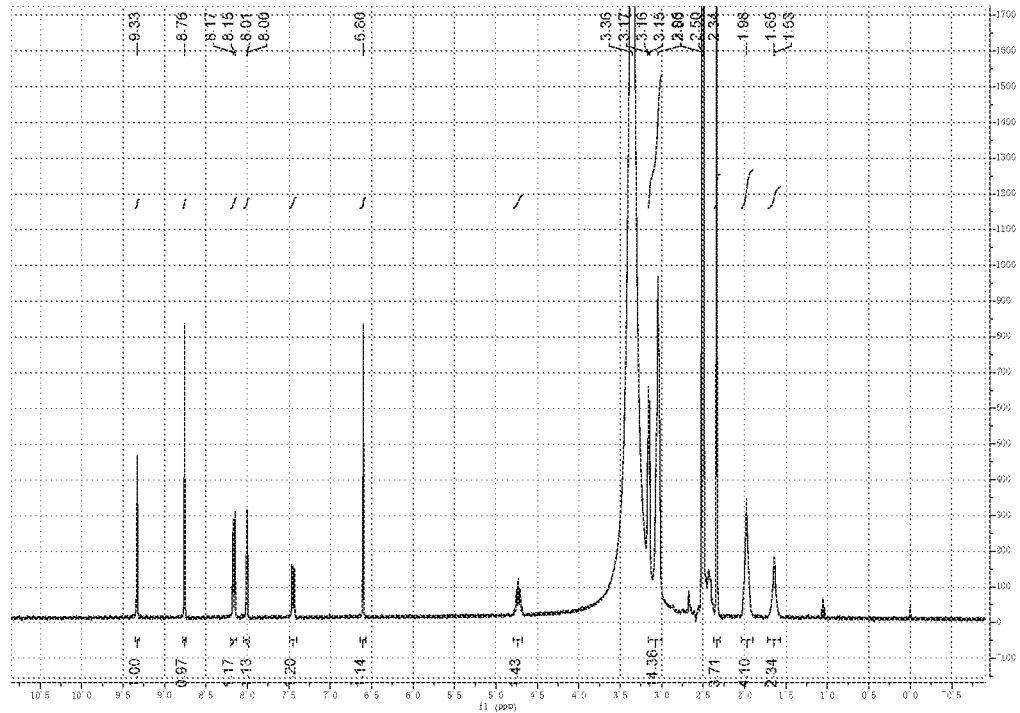
FIG. 6 $^1$H NMR spectrum of mono-succinate Form I.

The $^1$H NMR spectrum of the mono-succinate Form I produced in this example is displayed in FIG. 6. $^1$H NMR data is shown as following:

$^1$H NMR (400 MHz, DMSO) δ 9.33 (s, 1H), 8.76 (s, 1H), 8.16 (d, J=9.1 Hz, 1H), 8.00 (d, J=2.9 Hz, 1H), 7.45 (dd, J=9.1, 3.0 Hz, 1H), 6.60 (s, 1H), 4.79-4.68 (m, 1H), 3.16-3.00 (m, 14H), 2.34 (s, 4H), 1.98 (s, 4H), 1.64 (d, J=5.5 Hz, 2H). $^1$H NMR results show that Form I is a mono-succinate of compound I.

Figure 7:
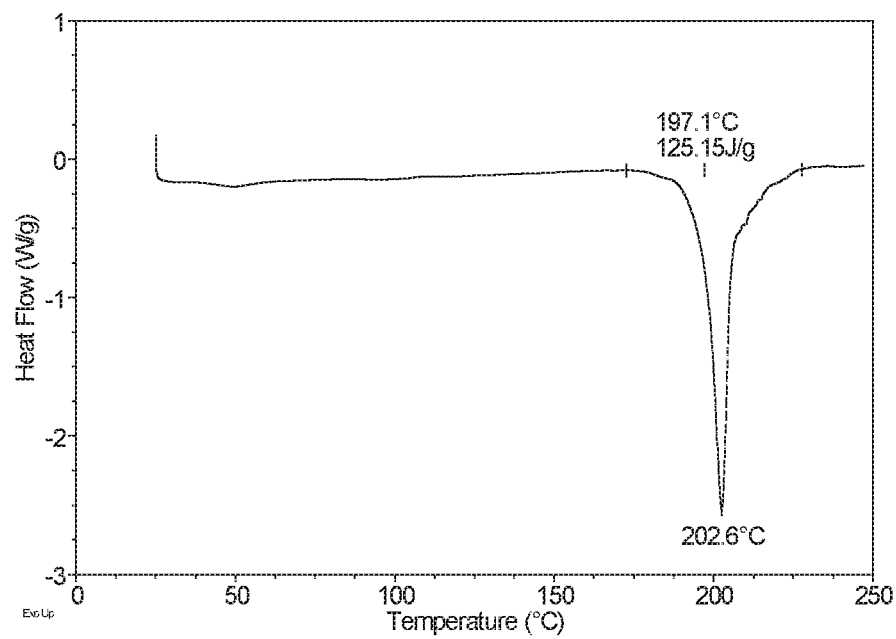
FIG. 7 DSC curve of mono-succinate Form I.

DSC curve of mono-succinate Form I was displayed in FIG. 7. Form I is an anhydrate, the DSC data showed an endothermic peak at 197° C. (onset temperature).

Figure 8:
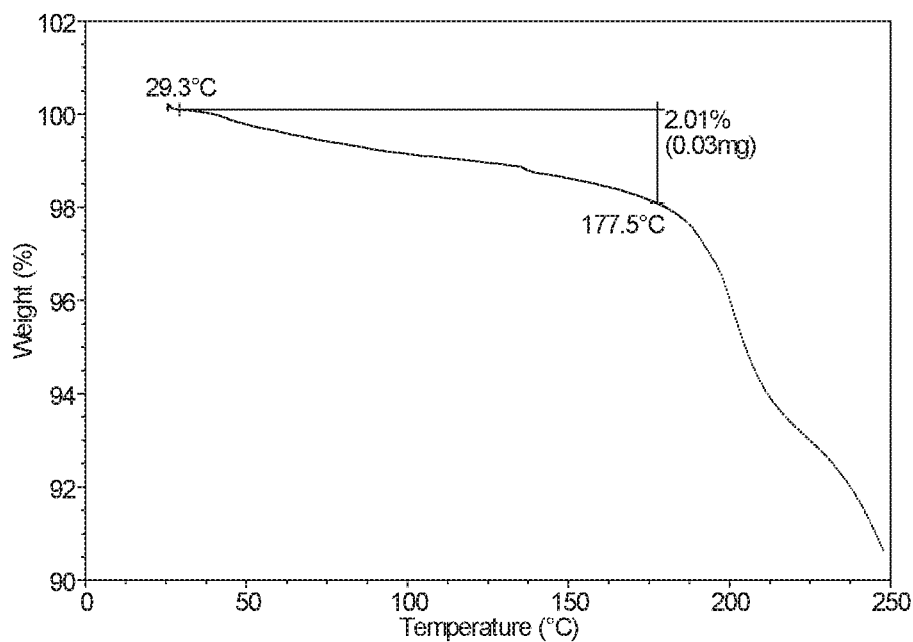
FIG. 8 TGA curve of mono-succinate Form I.

TGA curve of mono-succinate Form I was displayed in FIG. 8. The TGA data showed 2.0% weight loss up to 178° C.

EXAMPLE 6

Process for Preparing Mono-Succinate Form I:

3.1 mg of the non-hydrate form (prepared according to patent CN103201275A) was added into 0.5 mL of ethanol/n-heptane (v/v=4/1), then stirred at room temperature for 48 hours until solids precipitate out. The XRPD data of the mono-succinate Form I produced in this example is listed in Table 5.

TABLE 5

| 2theta | d spacing | Intensity % |
|---|---|---|
| 6.83 | 12.95 | 11.44 |
| 7.84 | 11.28 | 26.24 |
| 11.90 | 7.44 | 88.02 |
| 13.09 | 6.77 | 21.52 |
| 13.33 | 6.64 | 35.24 |
| 14.02 | 6.31 | 15.85 |
| 15.74 | 5.63 | 23.50 |
| 16.71 | 5.31 | 18.54 |
| 17.83 | 4.98 | 76.15 |
| 18.64 | 4.76 | 22.51 |
| 19.37 | 4.58 | 31.64 |
| 20.11 | 4.41 | 28.17 |
| 20.65 | 4.30 | 100.00 |
| 21.26 | 4.18 | 14.82 |
| 22.22 | 4.00 | 5.89 |
| 22.76 | 3.91 | 63.69 |
| 23.15 | 3.84 | 17.57 |
| 24.44 | 3.64 | 71.31 |
| 25.12 | 3.54 | 7.95 |
| 25.81 | 3.45 | 8.77 |
| 26.29 | 3.39 | 19.56 |
| 27.59 | 3.23 | 5.79 |
| 28.16 | 3.17 | 1.30 |
| 29.20 | 3.06 | 17.50 |
| 30.11 | 2.97 | 4.35 |
| 30.85 | 2.90 | 5.16 |
| 32.30 | 2.77 | 4.95 |
| 33.11 | 2.71 | 7.22 |
| 34.25 | 2.62 | 2.79 |
| 36.26 | 2.48 | 3.54 |

EXAMPLE 7

Stability of Mono-Succinate Form I of the Present Invention and Non-Hydrate Form in Patent CN103201275A at High Humidity:

About 10 mg of mono-succinate Form I of the present invention and non-hydrate form in patent CN103201275A were analyzed by DVS. The solid was tested by XRPD before and after hygroscopicity test. The DVS curve was displayed in FIG. 9, the XRPD overlay pattern before and after hygroscopicity test is displayed in FIG. 10. The result showed that it adsorbed 1.7% water at 25° C./90% RH, and Form I of the present invention did not change after hygroscopicity test. It indicated that Form I of the present invention was stable at high humidity. According to the data in patent CN103201275A, the non-hydrate form adsorbed 2.0% water at 25° C./90% RH, and 7.35% of the non-hydrate form converted to hydrate form. Furthermore, 0.52% of the non-hydrate form in patent CN103201275A converted to hydrate form at 25° C./80% RH.

Figure 9:
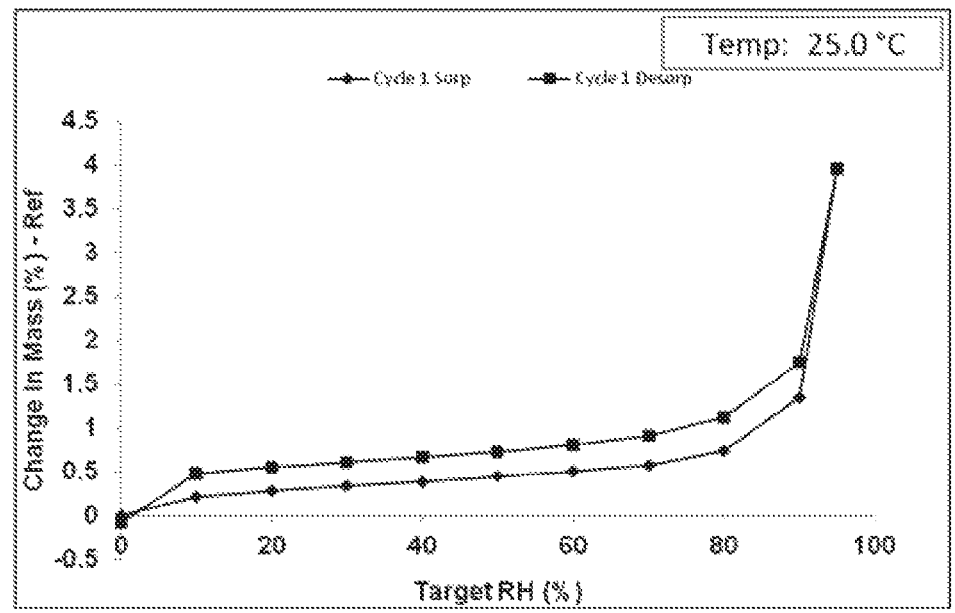
FIG. 9 DVS curve of mono-succinate Form I (0-95% RH cycle)
Figure 10:
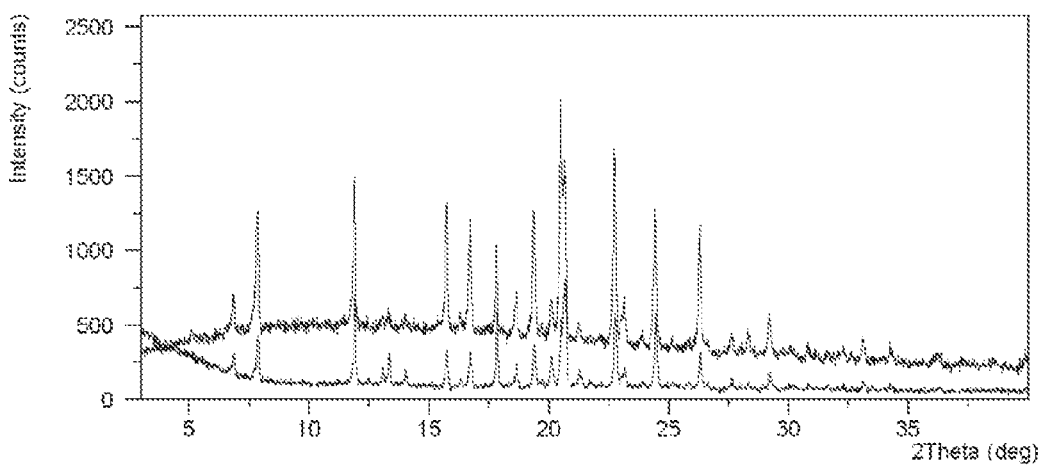
FIG. 10 XRPD overlay of mono-succinate Form I before and after hygroscopicity test (the pattern above is XRPD pattern of Form I before test, the pattern below is XRPD pattern of Form I after test)
Figure 11:
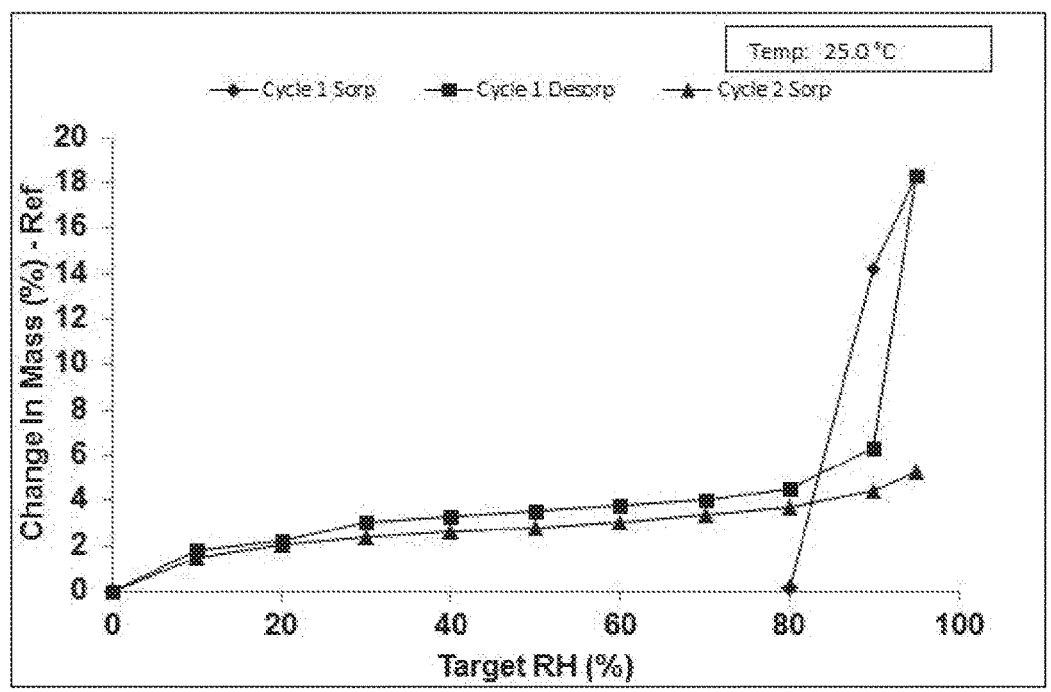
FIG. 11 DVS curve of mono-succinate non-hydrate form in CN103201275A (0-95% RH cycle)
Figure 12:
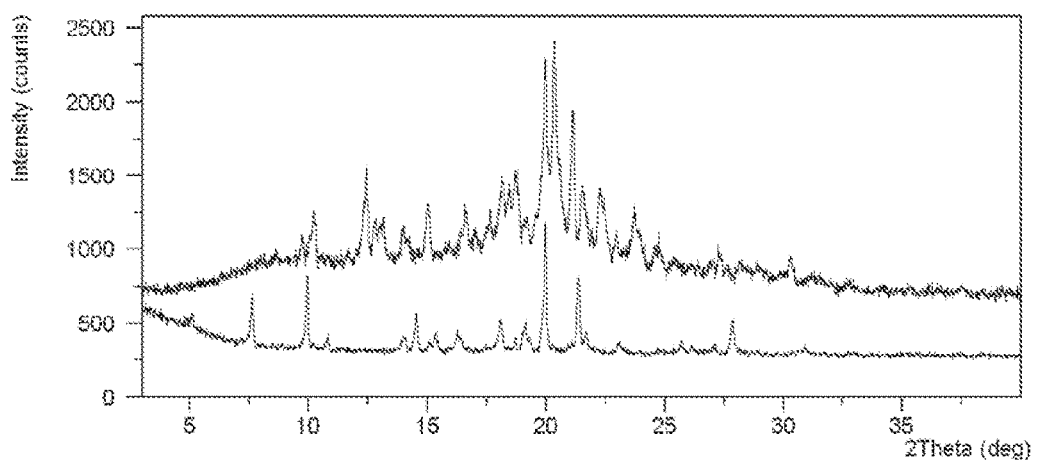
FIG. 12 XRPD overlay of mono-succinate non-hydrate form in patent CN103201275A before and after hygroscopicity test (the pattern above is XRPD pattern of mono-succinate in CN103201275A before test, the pattern below is XRPD pattern of mono-succinate in CN103201275A after test)

As shown in FIG. 9 and FIG. 10, Form I of the present invention adsorbed 4.0% water at 25° C./95% RH, and Form I of the present invention did not change after test. As shown in FIG. 11, the non-hydrate form adsorbed 18.3% water at 25° C./95% RH, and the solid form changed after test. The results indicated that Form I of the present invention was stable at high humidity and the solid form did not change, while the non-hydrate form in patent CN103201275A was not stable as it would easily have crystal transformation at high humidity.

EXAMPLE 8

Stability of Form I of the Present Invention and Mono-Succinate Non-Hydrate Form in Patent CN103201275A in Different Temperatures:

About 10 mg of the non-hydrate form in patent CN103201275A as starting form was added in different solvents or mixed solvents (v/v), then stirred at 5-50° C. for about 48 hours. Finally, the starting form converted to Form I. Solvents and temperature used in this example is in the following in table 6.

TABLE 6

| NO. | Starting Form | Temperature | Solvent/Mixed solvent (v/v) | Final Form |
|---|---|---|---|---|
| 1 | mono-succinate in patent CN103201275A | RT | Ethanol:n-heptane = 4:1 | mono-succinate Form I |
| 2 | mono-succinate in patent CN103201275A | 5° C. | Ethanol:n-heptane = 4:1 | mono-succinate Form I |
| 3 | mono-succinate in patent CN103201275A | 50° C. | Acetonitrile:water = 20:1 | mono-succinate Form I |
| 4 | mono-succinate in patent CN103201275A | 50° C. | THF:Methanol = 20:1 | mono-succinate Form I |

EXAMPLE 9

Figure 22:
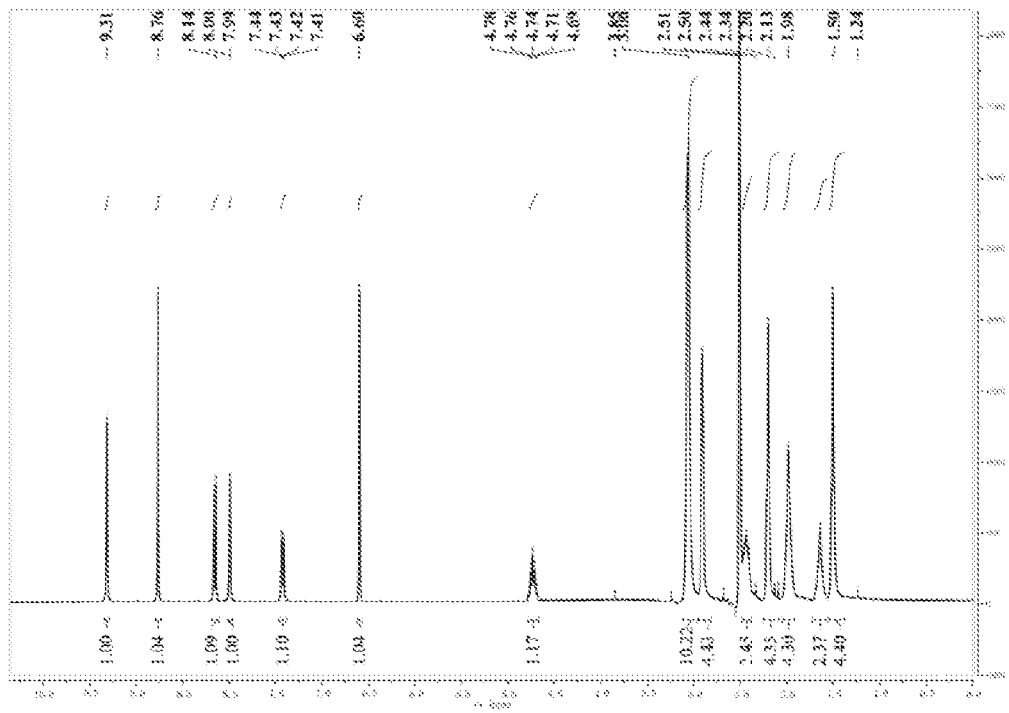
FIG. 22 $^1$H NMR spectrum of adipate Form A.

Process for Preparing Adipate:

200 mg of compound I freebase powder was added into 10.0 mL of acetone/water (v/v=19/1), and 68 mg of adipic acid was added to the solution, then stirred at room temperature, the solid was obtained. The $^1$H NMR spectrum is displayed in FIG. 22.

$^1$H NMR data of adipate Form A produced in this example is shown as following:

$^1$H NMR (400 MHz, DMSO) δ 9.31 (s, 1H), 8.76 (s, 1H), 8.15 (d, J=9.1 Hz, 1H), 7.99 (d, J=2.8 Hz, 1H), 7.42 (dd, J=9.1, 3.0 Hz, 1H), 6.60 (s, 1H), 4.78-4.67 (m, 1H), 3.06 (d, J=4.9 Hz, 10H), 2.95-2.82 (m, 4H), 2.48-2.38 (m, 2H), 2.25-2.09 (m, 4H), 1.98 (s, 4H), 1.64 (d, J=4.9 Hz, 2H), 1.54-1.38 (m, 4H).

Figure 13:
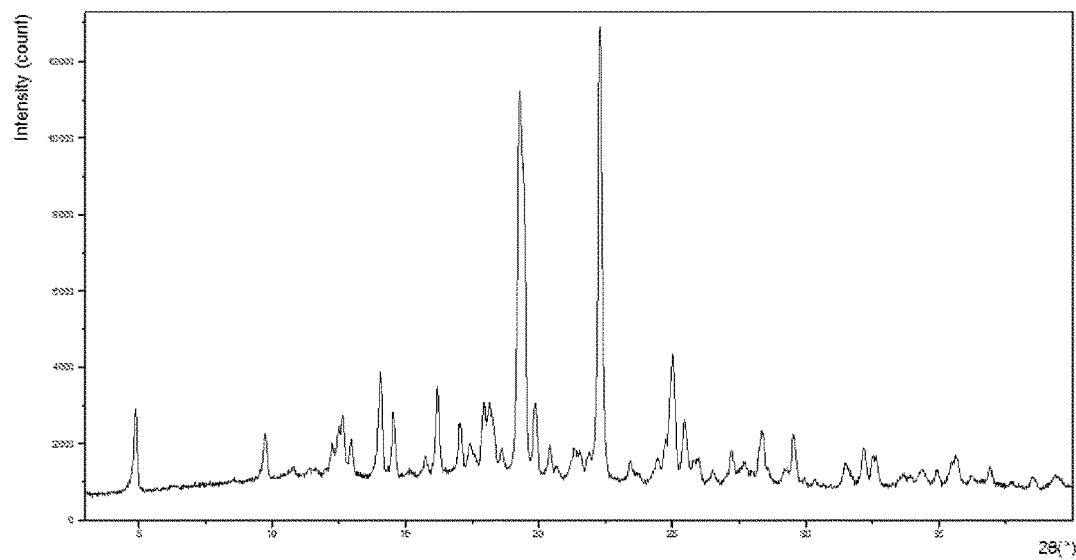
FIG. 13 XRPD pattern of adipate Form A.
Figure 14:
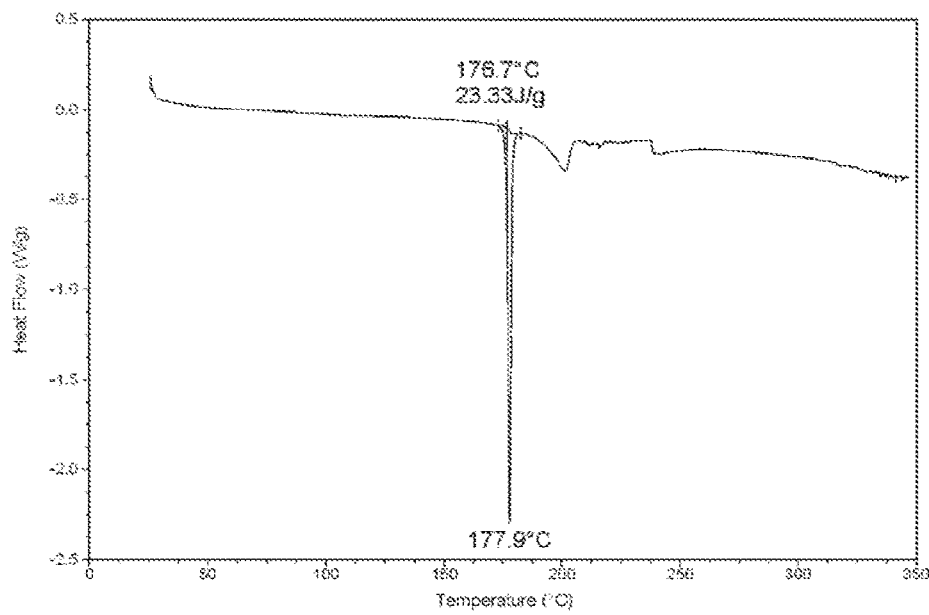
FIG. 14 DSC curve of adipate Form A.
Figure 15:
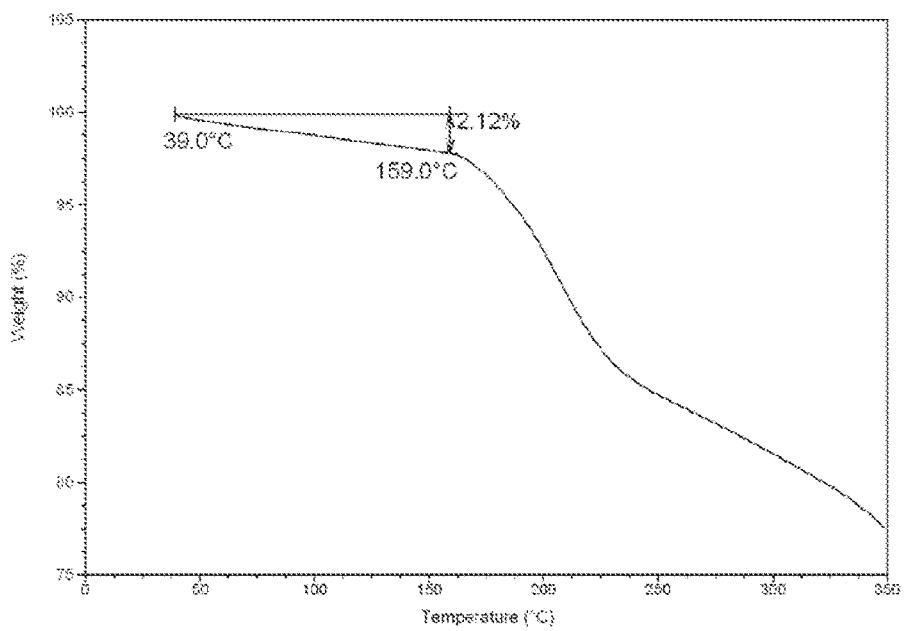
FIG. 15 TGA curve of adipate Form A.

The result shows the solid is adipate Form A. The XRPD data of the adipate Form A produced in this example are listed in Table 7. The XRPD pattern is displayed in FIG. 13, the DSC curve is displayed in FIG. 14, the TGA curve is displayed in FIG. 15.

TABLE 7

| 2theta | d spacing | Intensity % |
|---|---|---|
| 4.79 | 18.45 | 17.56 |
| 9.64 | 9.17 | 11.17 |
| 10.71 | 8.26 | 3.80 |
| 11.41 | 7.75 | 3.13 |
| 12.16 | 7.28 | 8.75 |
| 12.38 | 7.15 | 11.40 |
| 12.56 | 7.05 | 15.09 |
| 12.89 | 6.87 | 9.06 |
| 13.97 | 6.34 | 24.14 |
| 14.43 | 6.14 | 14.43 |
| 15.07 | 5.88 | 3.07 |
| 15.64 | 5.66 | 6.31 |
| 16.09 | 5.51 | 20.51 |
| 16.96 | 5.23 | 13.46 |
| 17.30 | 5.12 | 8.96 |
| 17.80 | 4.98 | 17.12 |
| 18.03 | 4.92 | 17.83 |
| 18.18 | 4.88 | 13.71 |
| 18.49 | 4.80 | 7.77 |
| 19.15 | 4.64 | 83.86 |
| 19.39 | 4.58 | 53.64 |
| 19.80 | 4.48 | 17.69 |
| 20.34 | 4.37 | 8.25 |
| 20.58 | 4.32 | 4.02 |
| 21.24 | 4.18 | 8.19 |
| 21.43 | 4.15 | 7.31 |
| 21.81 | 4.08 | 7.02 |
| 22.20 | 4.00 | 100.00 |
| 23.32 | 3.81 | 4.96 |
| 24.34 | 3.66 | 6.11 |
| 24.62 | 3.62 | 8.83 |
| 24.91 | 3.58 | 29.19 |
| 25.34 | 3.51 | 14.68 |
| 25.72 | 3.46 | 5.59 |
| 25.90 | 3.44 | 6.02 |
| 26.41 | 3.37 | 3.21 |
| 27.09 | 3.29 | 7.60 |
| 27.60 | 3.23 | 5.29 |
| 28.24 | 3.16 | 12.15 |
| 29.11 | 3.07 | 3.52 |
| 29.40 | 3.04 | 10.52 |
| 29.48 | 3.03 | 10.46 |
| 29.84 | 2.99 | 1.80 |
| 30.26 | 2.95 | 1.39 |
| 31.39 | 2.85 | 4.89 |
| 32.09 | 2.79 | 8.61 |
| 32.39 | 2.76 | 6.51 |
| 32.56 | 2.75 | 5.71 |
| 33.53 | 2.67 | 2.54 |
| 34.28 | 2.62 | 3.59 |

EXAMPLE 10

Process for Preparing Adipate:

10.3 mg of compound I freebase powder was added into 0.4 mL of acetone/water (v/v=19/1), and 3.9 mg of adipic acid was added to the solution, then stirred at room temperature, the solid was obtained.

The solid is adipate Form A after analysis. XRPD data is displayed in table 8

TABLE 8

| 2theta | d spacing | Intensity % |
|---|---|---|
| 4.85 | 18.22 | 100.00 |
| 9.67 | 9.15 | 19.12 |
| 12.37 | 7.16 | 11.38 |
| 12.58 | 7.04 | 12.33 |
| 13.97 | 6.34 | 25.90 |
| 14.47 | 6.12 | 13.90 |
| 16.09 | 5.51 | 30.88 |
| 16.94 | 5.23 | 7.33 |
| 17.82 | 4.98 | 13.28 |
| 18.11 | 4.90 | 8.57 |
| 19.11 | 4.64 | 52.72 |
| 19.36 | 4.59 | 63.62 |
| 19.79 | 4.49 | 9.60 |
| 20.34 | 4.37 | 8.80 |
| 21.38 | 4.16 | 5.23 |
| 22.20 | 4.00 | 83.50 |
| 24.94 | 3.57 | 18.93 |
| 25.34 | 3.51 | 9.62 |
| 28.24 | 3.16 | 5.76 |
| 29.46 | 3.03 | 6.03 |
| 31.41 | 2.85 | 3.22 |
| 32.13 | 2.79 | 5.49 |
| 32.50 | 2.76 | 3.51 |
| 35.54 | 2.53 | 2.90 |

EXAMPLE 11

Figure 23:
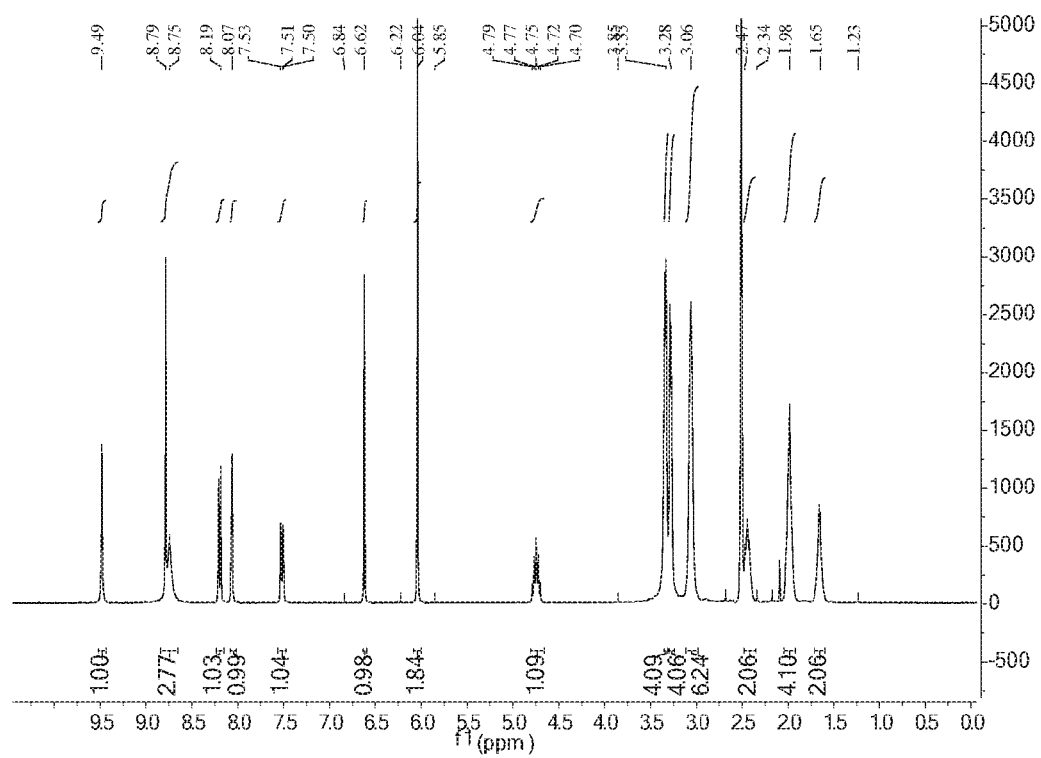
FIG. 23 $^1$H NMR spectrum of maleate Form A.

Process for Preparing Maleate:

200.63 mg of compound I freebase powder was added into 10.0 mL of acetone/water (v/v=19/1), and 56 mg of maleic acid was added to the solution, then stirred at room temperature, the solid was obtained, The $^1$H NMR spectrum is displayed in FIG. 23.

$^1$H NMR data of the maleate Form A produced in this example are shown as following:

$^1$H NMR (400 MHz, DMSO) δ 9.49 (s, 1H), 8.77 (s, 1H), 8.20 (d, J=9.1 Hz, 1H), 8.07 (d, J=2.8 Hz, 1H), 7.52 (dd, J=9.1, 2.8 Hz, 1H), 6.62 (s, 1H), 6.04 (s, 2H), 4.80-4.66 (m, 1H), 3.34 (d, J=5.6 Hz, 4H), 3.28 (d, J=5.3 Hz, 4H), 3.06 (s, 6H), 2.48-2.35 (m, 2H), 1.98 (s, 4H), 1.65 (d, J=5.3 Hz, 2H).

Figure 16:
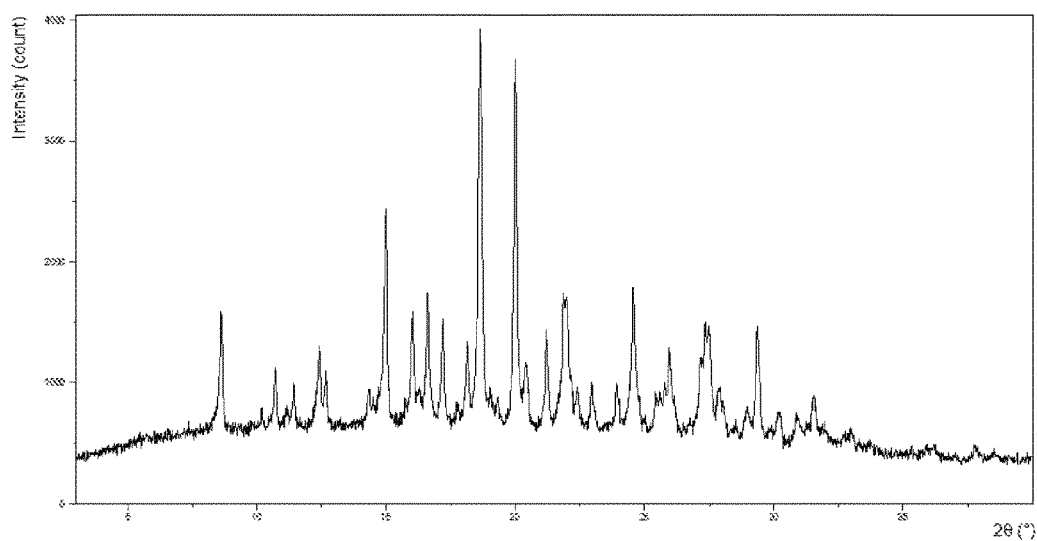
FIG. 16 XRPD pattern of maleate Form A.
Figure 17:
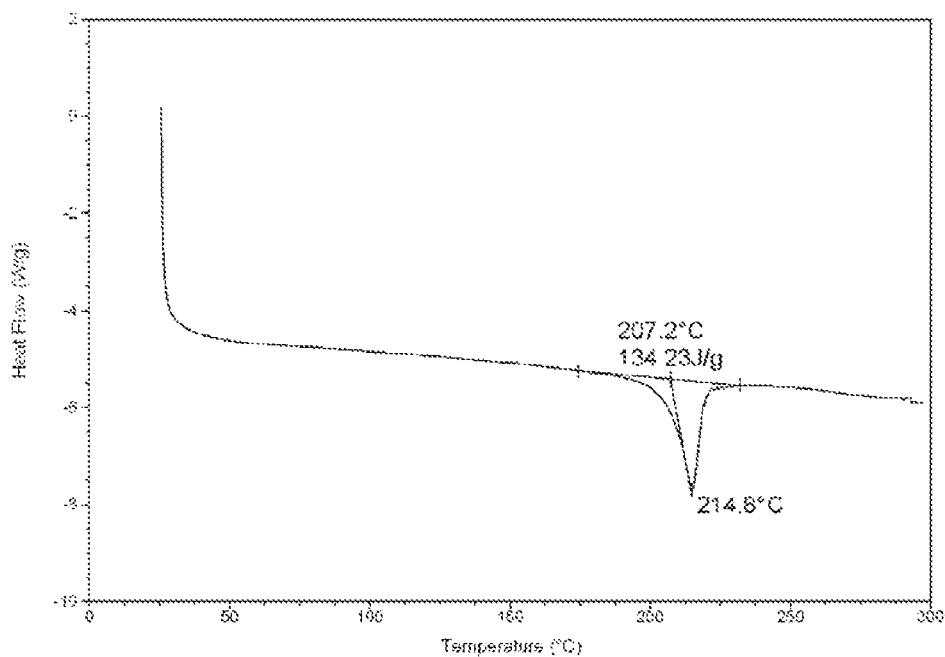
FIG. 17 DSC curve of maleate Form A.
Figure 18:
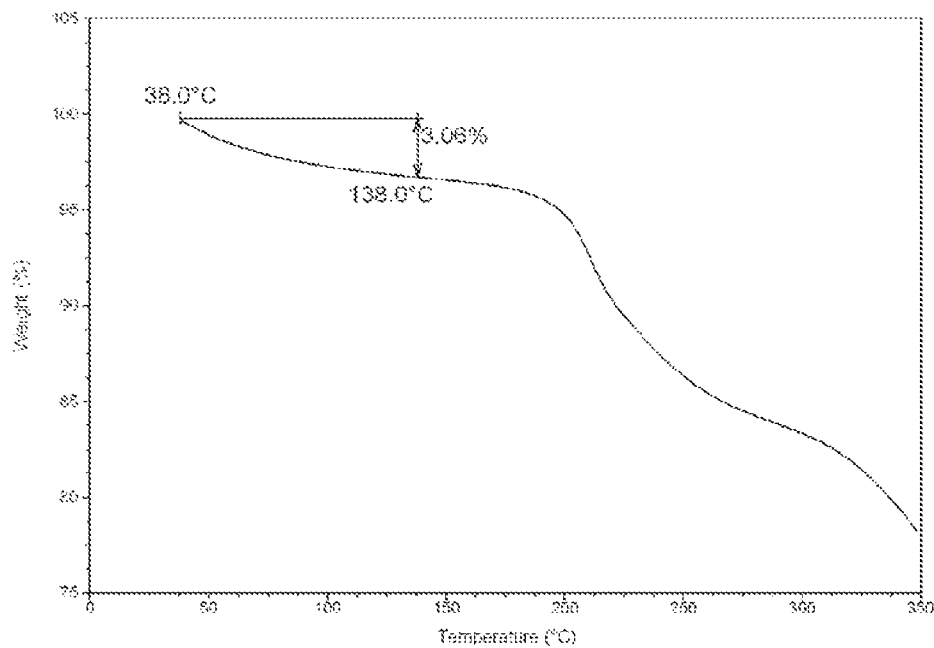
FIG. 18 TGA curve of maleate Form A.

The result shows the solid is maleate Form A. The XRPD data of the maleate Form A is listed in Table 9. The XRPD pattern is displayed in FIG. 16, the DSC curve is displayed in FIG. 17, the TGA curve is displayed in FIG. 18.

TABLE 9

| 2theta | d spacing | Intensity % |
|---|---|---|
| 8.52 | 10.38 | 30.01 |
| 10.64 | 8.31 | 16.43 |
| 10.99 | 8.05 | 3.98 |
| 11.35 | 7.80 | 13.13 |
| 12.35 | 7.17 | 21.68 |
| 12.59 | 7.03 | 15.42 |
| 14.25 | 6.22 | 11.75 |
| 14.90 | 5.95 | 56.02 |
| 15.93 | 5.56 | 28.44 |

TABLE 9-continued

| 2theta | d spacing | Intensity % |
|---|---|---|
| 16.53 | 5.36 | 36.61 |
| 17.10 | 5.19 | 29.08 |
| 17.67 | 5.02 | 8.92 |
| 18.05 | 4.91 | 23.39 |
| 18.55 | 4.78 | 100.00 |
| 18.94 | 4.69 | 13.24 |
| 19.22 | 4.62 | 11.29 |
| 19.90 | 4.46 | 94.35 |
| 20.35 | 4.36 | 19.29 |
| 21.13 | 4.20 | 25.99 |
| 21.78 | 4.08 | 36.87 |
| 21.93 | 4.05 | 35.06 |
| 22.31 | 3.98 | 13.67 |
| 22.85 | 3.89 | 14.35 |
| 23.83 | 3.73 | 15.82 |
| 24.47 | 3.64 | 38.79 |
| 25.35 | 3.51 | 12.11 |
| 25.87 | 3.44 | 23.90 |
| 27.07 | 3.29 | 21.86 |
| 27.42 | 3.25 | 27.86 |
| 27.79 | 3.21 | 14.66 |
| 28.88 | 3.09 | 9.88 |
| 29.26 | 3.05 | 30.60 |
| 30.14 | 2.97 | 9.28 |
| 30.80 | 2.90 | 8.50 |
| 31.49 | 2.84 | 13.38 |
| 32.82 | 2.73 | 4.33 |
| 36.00 | 2.49 | 1.81 |
| 37.70 | 2.39 | 3.06 |
| 38.44 | 2.34 | 1.34 |

EXAMPLE 12

Process for Preparing Maleate:

10.3 mg of compound I freebase powder was added into 0.4 mL of acetone, and 2.8 mg of maleic acid was added to the solution, then stirred at room temperature, the solid was obtained.

The solid is maleate Form A after analysis. XRPD data is displayed in table 10.

TABLE 10

| 2theta | d spacing | Intensity % |
|---|---|---|
| 5.41 | 16.33 | 37.33 |
| 7.81 | 11.32 | 33.48 |
| 8.54 | 10.36 | 37.61 |
| 10.65 | 8.31 | 22.54 |
| 12.35 | 7.17 | 29.59 |
| 14.90 | 5.95 | 71.33 |
| 15.95 | 5.56 | 33.17 |
| 16.54 | 5.36 | 35.61 |
| 17.10 | 5.18 | 33.04 |
| 18.07 | 4.91 | 26.12 |
| 18.53 | 4.79 | 100.00 |
| 19.92 | 4.46 | 97.61 |
| 21.13 | 4.21 | 22.94 |
| 21.88 | 4.06 | 42.29 |
| 24.51 | 3.63 | 32.45 |
| 25.95 | 3.43 | 15.94 |
| 27.29 | 3.27 | 21.96 |
| 29.28 | 3.05 | 26.98 |
| 31.58 | 2.83 | 7.08 |

EXAMPLE 13

Figure 24:
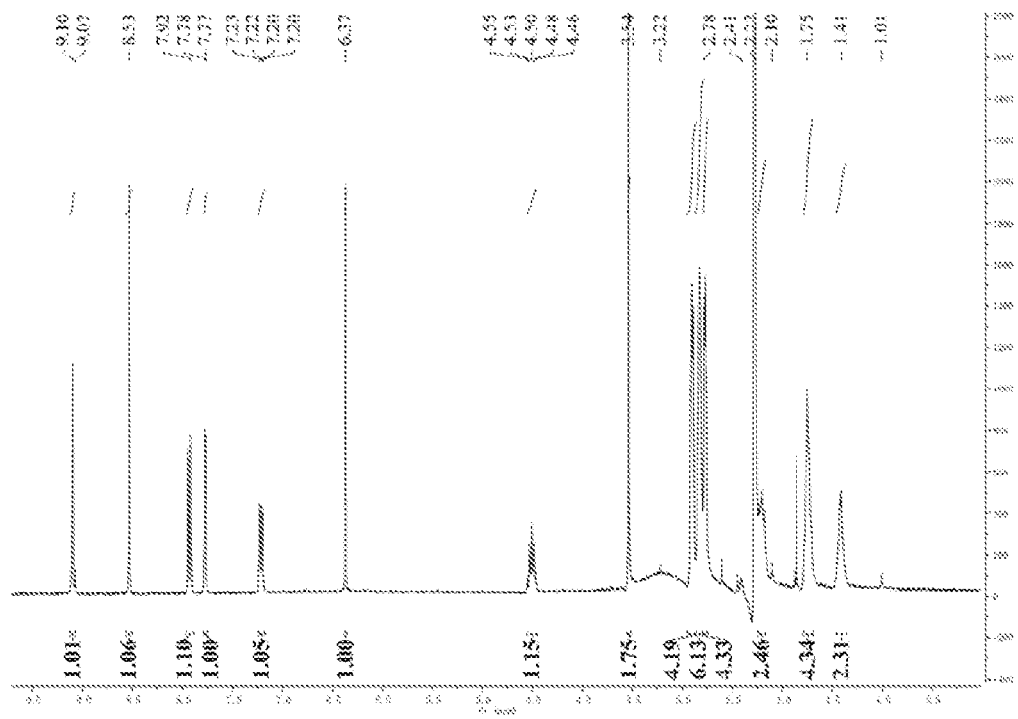
FIG. 24 $^1$H NMR spectrum of glycollate Form A.

Process for Preparing Glycollate:

199.0 mg of compound I freebase powder was added into 10.0 mL of acetone/water (v/v=19/1), and 34.0 mg of glycolic acid was added to the solution, then stirred at room temperature, the solid was obtained. The H$^1$NMR spectrum is displayed in FIG. 24.

$^1$H NMR data of glycollate Form A produced in this example is shown as following:

$^1$H NMR (400 MHz, DMSO) δ 9.09 (d, J=10.7 Hz, 1H), 8.53 (s, 1H), 7.93 (d, J=9.1 Hz, 1H), 7.78 (d, J=2.9 Hz, 1H), 7.21 (dd, J=9.1, 2.9 Hz, 1H), 6.37 (s, 1H), 4.55-4.45 (m, 1H), 3.54 (s, 2H), 2.95-2.87 (m, 4H), 2.83 (s, 6H), 2.79-2.74 (m, 4H), 2.24-2.17 (m, 2H), 1.75 (s, 4H), 1.41 (d, J=5.0 Hz, 2H).

Figure 19:
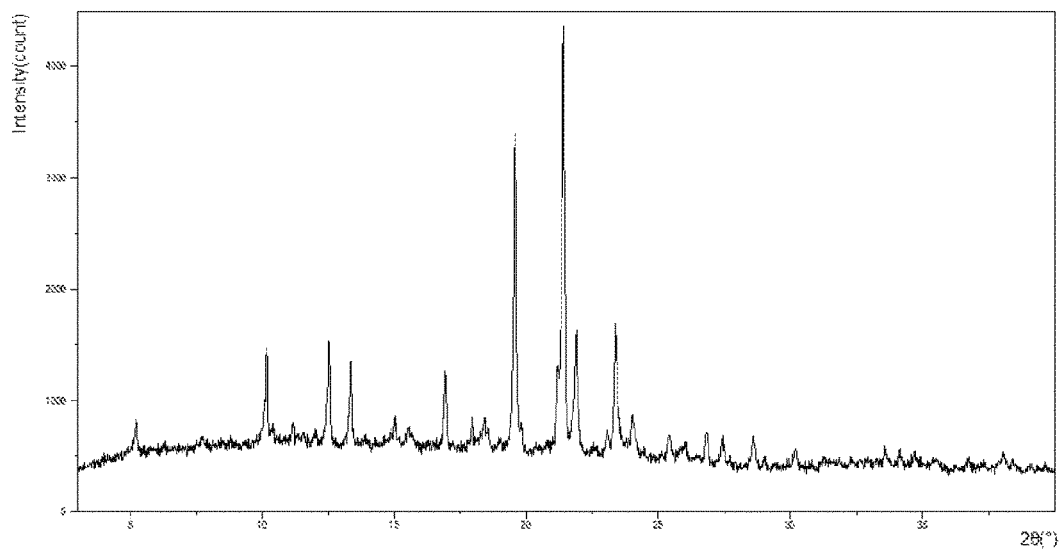
FIG. 19 XRPD pattern of glycollate Form A.
Figure 20:
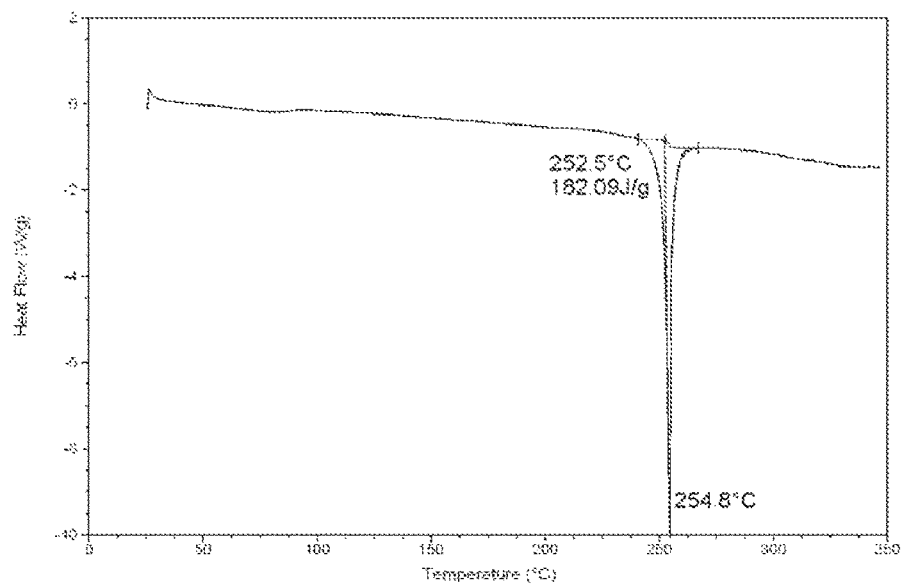
FIG. 20 DSC curve of glycollate Form A.
Figure 21:
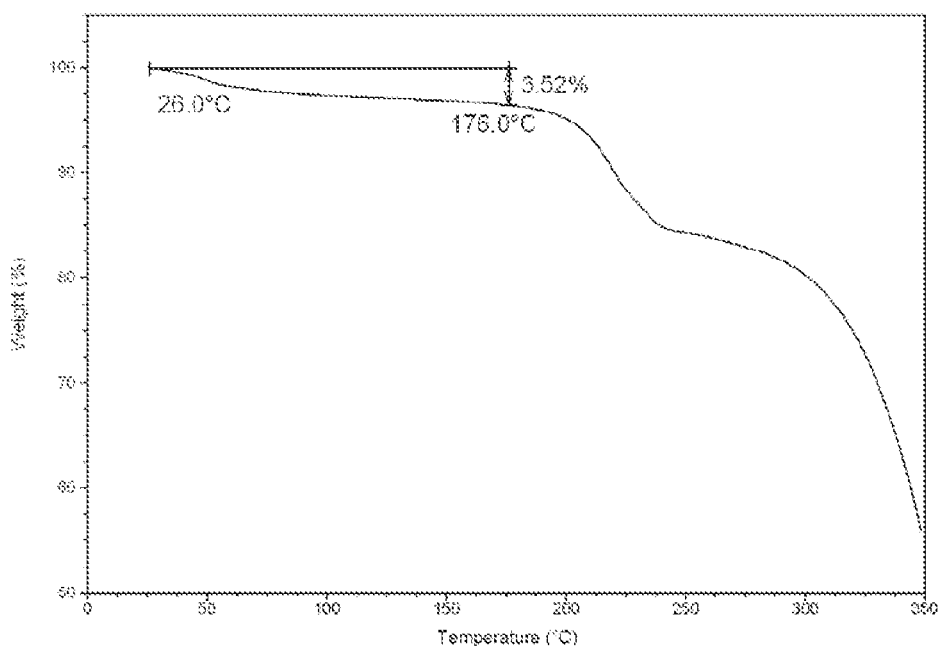
FIG. 21 TGA curve of glycollate Form A.

The result shows the solid is glycollate Form A. The XRPD data of the glycollate Form A is listed in Table 11. The XRPD pattern is displayed in FIG. 19, the DSC curve is displayed in FIG. 20, the TGA curve is displayed in FIG. 21,

TABLE 11

| 2theta | d spacing | Intensity % |
|---|---|---|
| 5.13 | 17.22 | 9.69 |
| 7.61 | 11.61 | 5.72 |
| 10.06 | 8.79 | 26.70 |
| 10.29 | 8.60 | 9.05 |
| 11.08 | 7.99 | 8.79 |
| 12.43 | 7.12 | 27.49 |
| 13.26 | 6.68 | 23.74 |
| 14.90 | 5.95 | 10.46 |
| 15.42 | 5.75 | 8.40 |
| 16.82 | 5.27 | 21.30 |
| 17.84 | 4.97 | 9.39 |
| 18.30 | 4.85 | 10.54 |
| 19.46 | 4.56 | 74.36 |
| 21.08 | 4.21 | 21.65 |
| 21.28 | 4.17 | 100.00 |
| 21.79 | 4.08 | 30.27 |
| 22.55 | 3.94 | 4.22 |
| 22.95 | 3.87 | 7.78 |
| 23.26 | 3.82 | 31.82 |
| 23.90 | 3.72 | 11.86 |
| 25.31 | 3.52 | 7.49 |
| 25.92 | 3.44 | 5.24 |
| 26.72 | 3.34 | 7.72 |
| 27.04 | 3.30 | 1.06 |
| 27.30 | 3.27 | 6.40 |
| 28.49 | 3.13 | 7.19 |
| 28.92 | 3.09 | 2.10 |
| 30.10 | 2.97 | 4.36 |
| 32.21 | 2.78 | 2.03 |
| 33.47 | 2.68 | 4.76 |
| 34.04 | 2.63 | 3.14 |
| 34.57 | 2.59 | 2.92 |
| 35.49 | 2.53 | 1.49 |
| 36.61 | 2.45 | 1.93 |
| 37.98 | 2.37 | 2.93 |

EXAMPLE 14

Process for Preparing Glycollate:

10.3 mg of compound I freebase powder was added into 0.4 mL of acetone/water (v/v=19/1), and 4.2 mg of glycolic acid was added to the solution, then stirred at room temperature, the solid was obtained.

The solid is glycollate Form A after analysis. XRPD data is displayed in table 12.

TABLE 12

| 2theta | d spacing | Intensity % |
|---|---|---|
| 5.11 | 17.30 | 21.55 |
| 10.03 | 8.82 | 35.40 |
| 11.03 | 8.02 | 5.25 |

TABLE 12-continued

| 2theta | d spacing | Intensity % |
|---|---|---|
| 12.40 | 7.14 | 33.03 |
| 13.23 | 6.69 | 26.09 |
| 14.90 | 5.95 | 8.26 |
| 15.40 | 5.75 | 4.84 |
| 16.77 | 5.29 | 17.99 |
| 17.83 | 4.98 | 7.39 |
| 18.28 | 4.85 | 6.80 |
| 19.45 | 4.56 | 87.19 |
| 20.65 | 4.30 | 4.90 |
| 21.24 | 4.18 | 100.00 |
| 21.76 | 4.08 | 37.62 |
| 22.94 | 3.88 | 9.03 |
| 23.22 | 3.83 | 29.44 |
| 23.91 | 3.72 | 14.57 |
| 25.29 | 3.52 | 6.02 |
| 25.90 | 3.44 | 5.66 |
| 26.73 | 3.34 | 8.95 |
| 27.27 | 3.27 | 6.00 |
| 28.49 | 3.13 | 8.21 |
| 28.94 | 3.09 | 2.58 |
| 30.09 | 2.97 | 5.59 |
| 31.16 | 2.87 | 3.39 |
| 33.48 | 2.68 | 5.30 |
| 34.10 | 2.63 | 3.59 |
| 34.56 | 2.60 | 3.88 |
| 35.34 | 2.54 | 2.36 |
| 36.59 | 2.46 | 2.50 |
| 37.95 | 2.37 | 3.36 |

EXAMPLE 15

Stability of Crystalline Salt Forms of Compound I:

Two samples prepared by example 9, example 11 and example 13 were stored for 30 days under 25° C./60% RH and 40° C./75% RH. The samples before and after storage were tested by XRPD, the results were summarized in table 13.

TABLE 13

Figure 25:
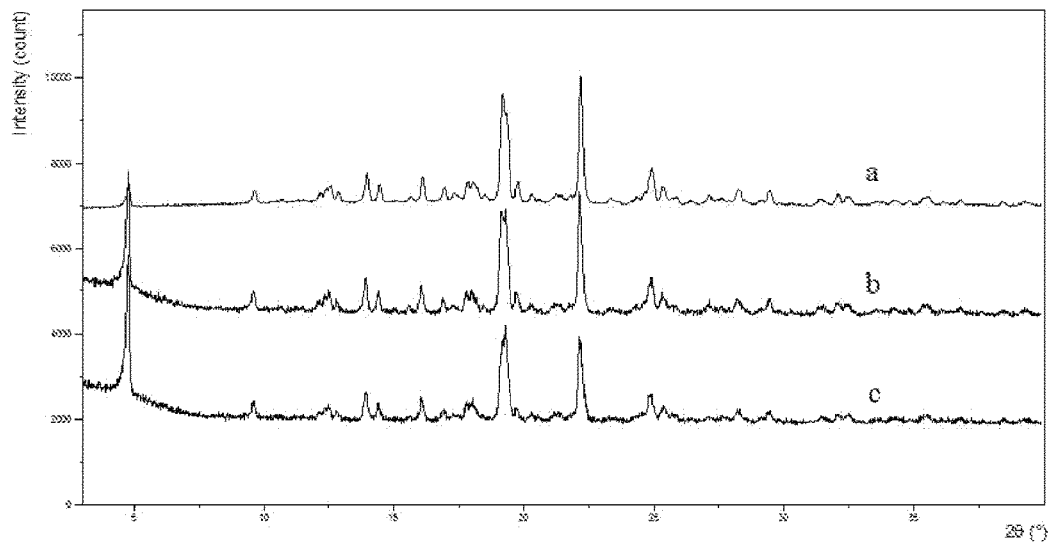
FIG. 25 XRPD overlay of the stability of adipate Form A (a is the XRPD pattern of initial sample, b is XRPD pattern of adipate Form A placing at 25° C./60% RH for 30 days, c is XRPD pattern of adipate Form A placing at 40° C./75% RH for 30 days)
Figure 26:
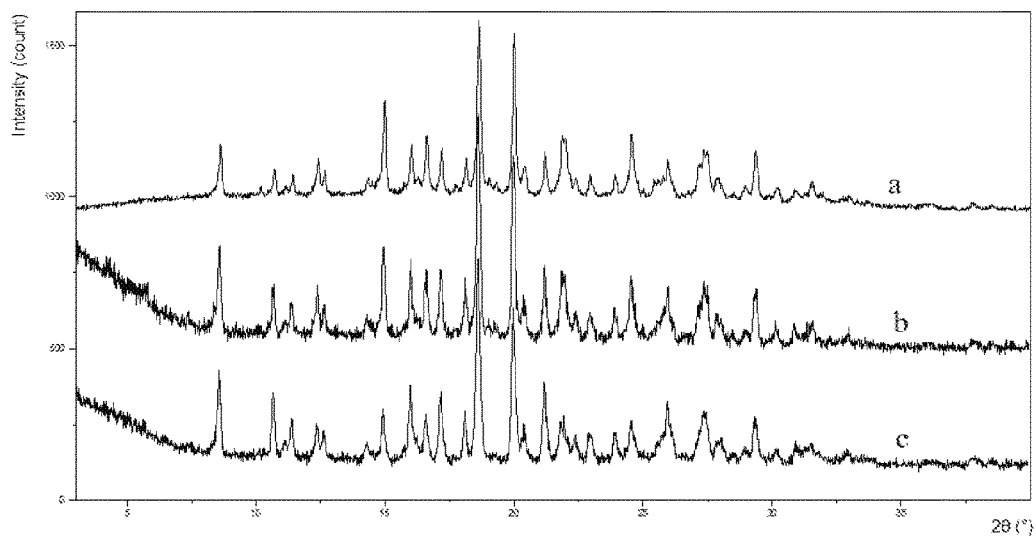
FIG. 26 XRPD overlay of the stability of maleate Form A (a is the XRPD pattern of initial sample, b is XRPD pattern of maleate Form A placing at 25° C./60% RH for 30 days, c is XRPD pattern of maleate Form A placing at 40° C./75% RH for 30 days)
Figure 27:
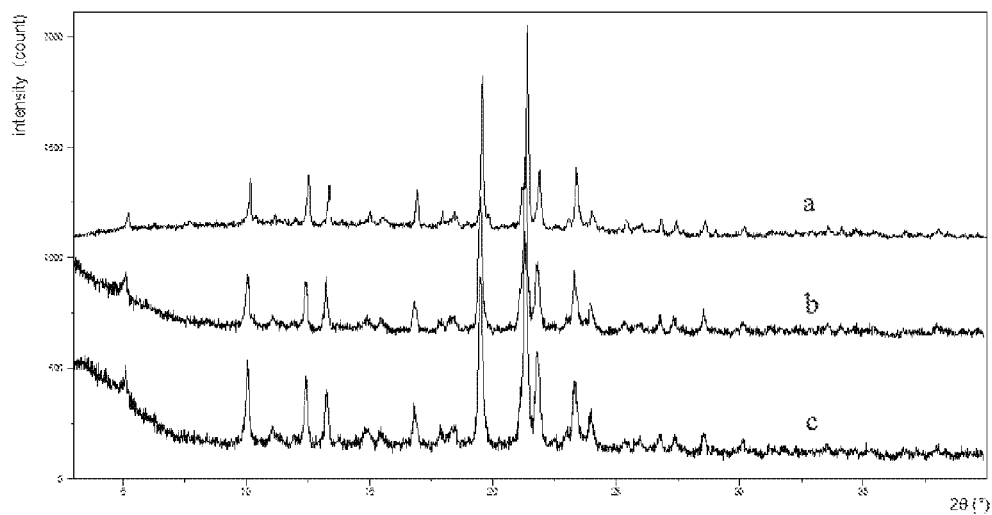
FIG. 27 XRPD overlay of the stability of glycollate Form A (a is the XRPD pattern of initial sample, b is XRPD pattern of glycollate Form A placing at 25° C./60% RH for 30 days, c is XRPD pattern of glycollate Form A placing at 40° C./75% RH for 30 days)

| Starting Form | Storage Condition | Storage Time | Solid Form | HPLC Purity (%) |
|---|---|---|---|---|
| Adipate Form A (FIG. 25a) | 25° C./60% RH | 30 days | No Change (FIG. 25b) | 99.1 |
| Adipate Form A (FIG. 25a) | 40° C./75% RH | 30 days | No Change (FIG. 25c) | 98.9 |
| Maleate Form A (FIG. 26a) | 25° C./60% RH | 30 days | No Change (FIG. 26b) | 99.3 |
| Maleate Form A (FIG. 26a) | 40° C./75% RH | 30 days | No Change (FIG. 26c) | 99.3 |
| Glycollate TypeA (FIG. 27a) | 25° C./60% RH | 30 days | No Change (FIG. 27b) | 99.7 |
| Glycollate TypeA (FIG. 27a) | 40° C./75% RH | 30 days | No Change (FIG. 27c) | 99.6 |

The results indicate that the crystalline salt forms of compound I did not change after 30 days. In conclusion, the result proves excellent stability of crystalline salt forms of compound I.

EXAMPLE 16

Figure 28:
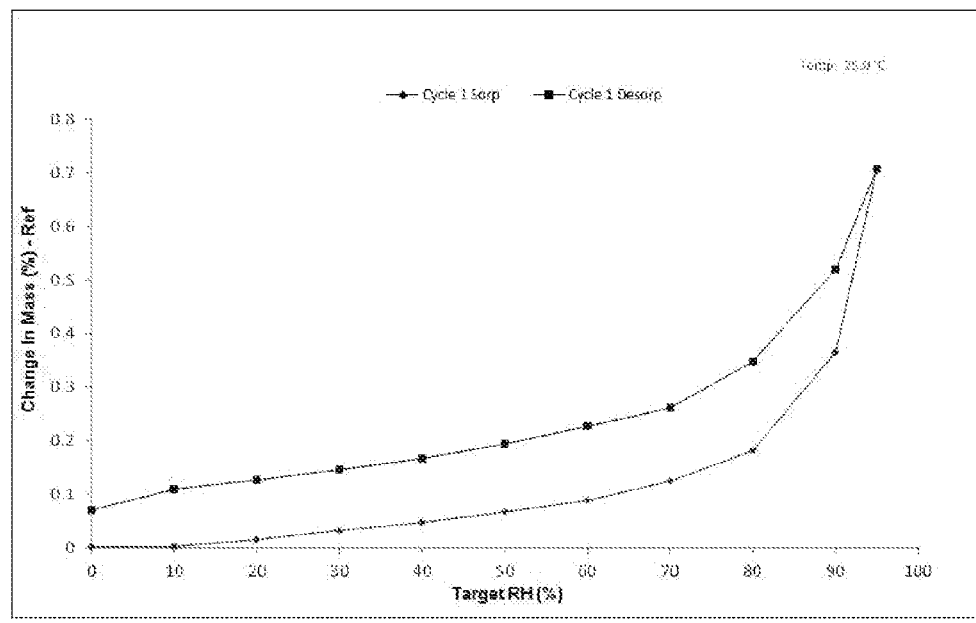
FIG. 28 DVS curve of adipate Form A (0-95% RH cycle)
Figure 29:
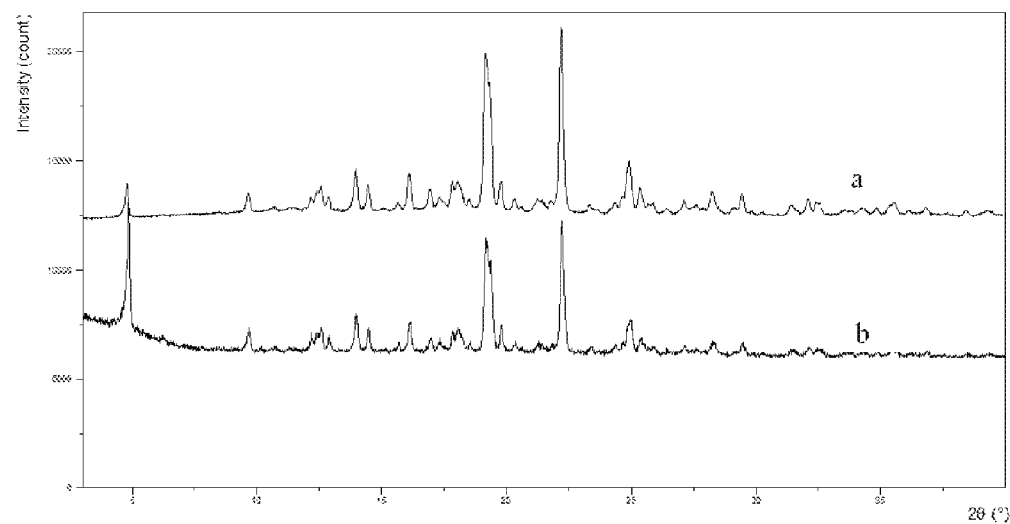
FIG. 29 XRPD overlay of adipate Form A before and after hygroscopicity test (a is XRPD pattern of adipate Form A before test, b is XRPD pattern of adipate Form A after test)
Figure 30:
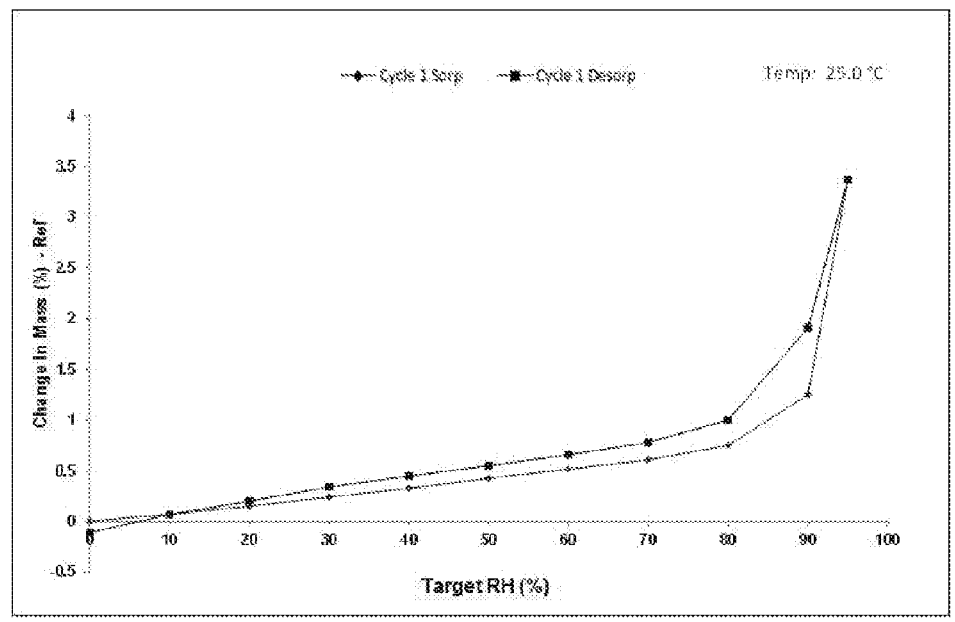
FIG. 30 DVS curve of maleate Form A (0-95% RH cycle)
Figure 31:
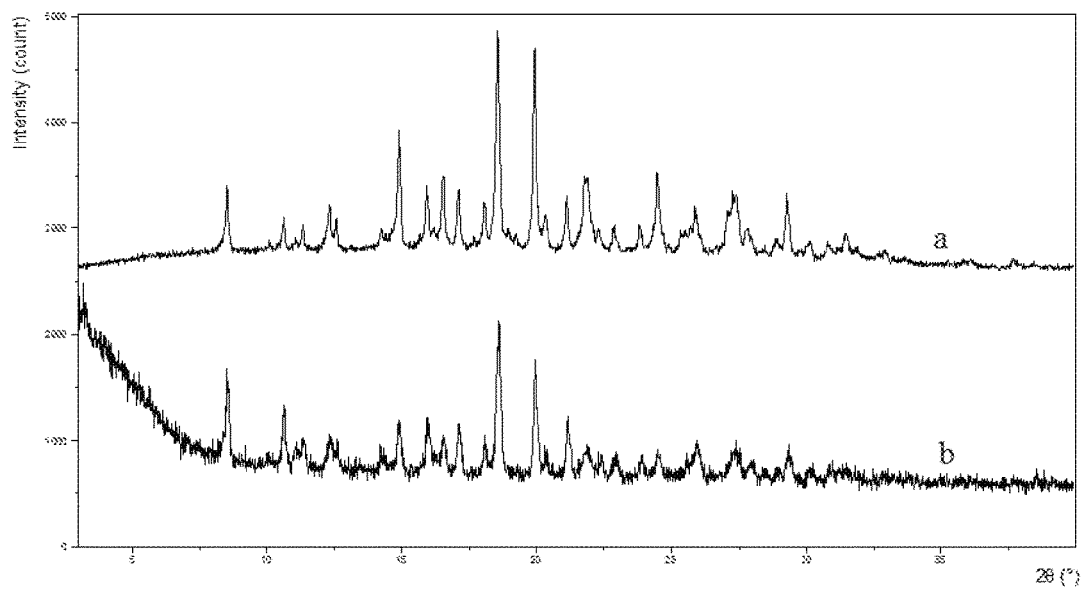
FIG. 31 XRPD overlay of maleate Form A before and after hygroscopicity test (a is XRPD pattern of maleate Form A before test, b is XRPD pattern of maleate Form A after test)
Figure 32:
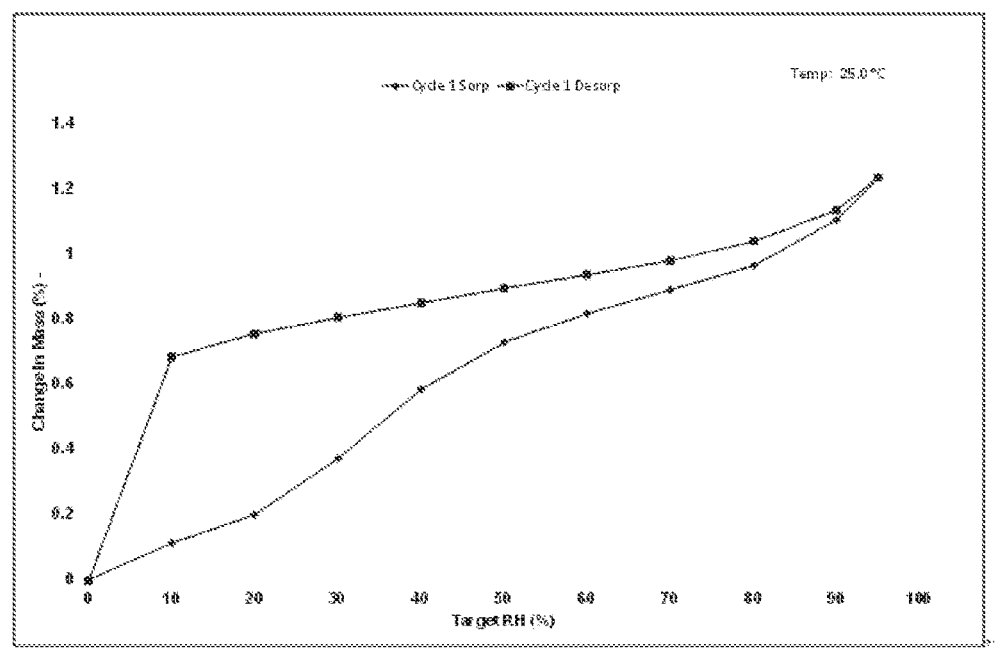
FIG. 32 DVS curve of glycollate Form A (0-95% RH cycle)
Figure 33:
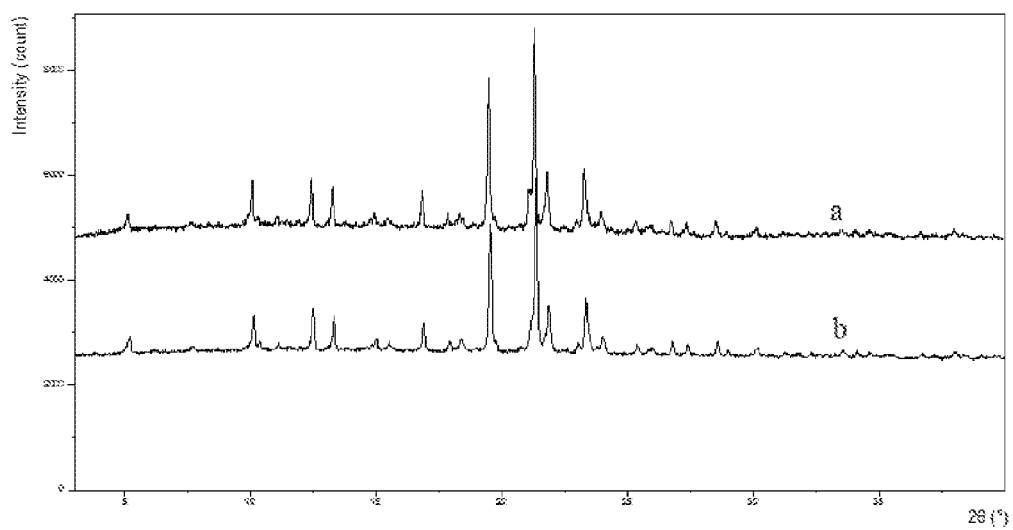
FIG. 33 XRPD overlay of glycollate Form A before and after hygroscopicity test (a is XRPD pattern of glycollate Form A before test, b is XRPD pattern of glycollate Form A after test)
Figure 34:
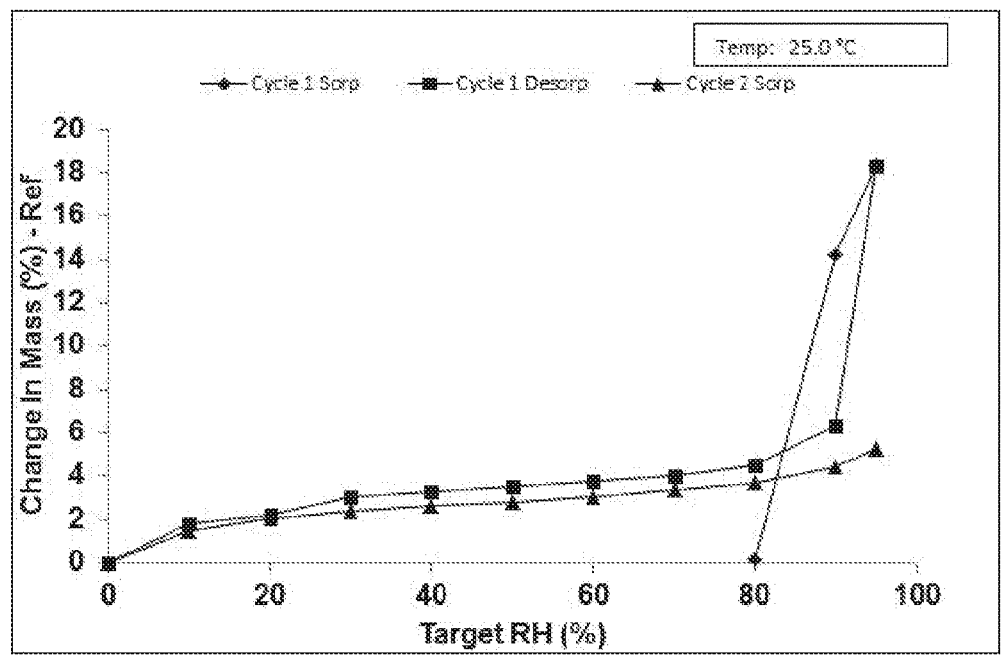
FIG. 34 DVS curve of mono-succinate non-hydrate form in CN103201275A (0-95% RH cycle)
Figure 35:
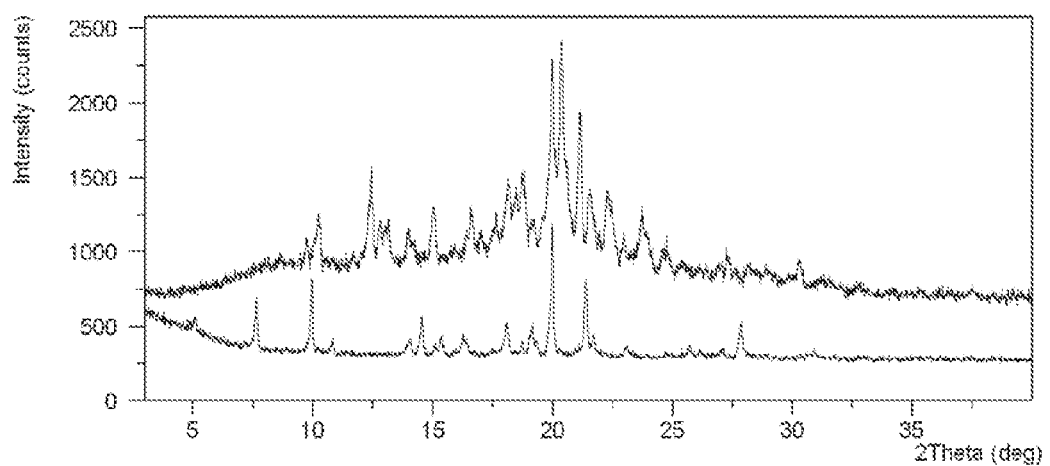
FIG. 35 XRPD overlay of mono-succinate non-hydrate form in patent CN103201275A before and after hygroscopicity test (the pattern below is XRPD pattern before test, the pattern above is XRPD pattern after test, form changed)

Stability of Salts in Present Invention and Mono-Succinate in Patent CN103201275A at High Humidity:

About 10 mg of adipate Form A, maleate Form A, glycollate Form A and mono-succinate non-hydrate form in patent CN103201275A were analyzed by DVS. The solid was tested by XRPD before and after hygroscopicity test. The results were displayed in table 14, the DVS curve of adipate Form A was displayed in FIG. 28, the XRPD overlay pattern is displayed in FIG. 29. The DVS curve of maleate Form A was displayed in FIG. 30, the XRPD overlay pattern was displayed in FIG. 31. The DVS curve of glycollate Form A was displayed in FIG. 32, the XRPD overlay pattern was displayed in FIG. 33. The DVS curve of non-hydrate form in patent CN103201275A was displayed in FIG. 34, the XRPD overlay pattern was displayed in FIG. 35 (the pattern below is before DVS, the pattern above is after DVS).

TABLE 14

| Starting Form | Water absorption at 25° C./95% RH | Change after DVS |
|---|---|---|
| adipate Form A | 0.7 | No change |
| maleate Form A | 3.4 | No change |
| glycollate Form A | 1.2 | No change |
| mono-succinate non-hydrate form in patent CN103201275A | 18.3 | Change |

The results indicated that adipate Form A, maleate Form A and glycollate Form A were stable at high humidity and the solid form did not change. While the non-hydrate form in patent CN103201275A was not stable as it changed in high humidity.

The examples described above are only for illustrating the technical concepts and features of the present invention, and intended to make those skilled in the art being able to understand the present invention and thereby implement it, and should not be concluded to limit the protective scope of this invention. Any equivalent variations or modifications according to the spirit of the present invention should be covered by the protective scope of the present invention.

The invention claimed is:

1. A crystalline mono-succinate Form I of compound I,

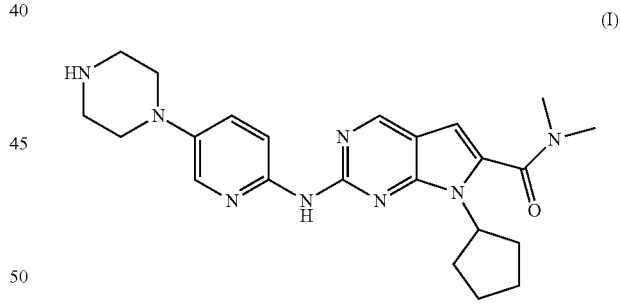

(I)

wherein the X-ray powder diffraction pattern of the crystalline Form I shows characteristic peaks at 2theta values of 11.9°±0.2°, 19.4°±0.2°, 20.6°±0.2°.

2. The crystalline Form I according to claim 1, wherein the X-ray powder diffraction pattern of the crystalline Form I shows one or two or three of the characteristic peaks at 2theta values of 22.7°±0.2°, 24.4°±0.2°, 26.3°±0.2°.

3. The crystalline Form I according to claim 2, wherein the X-ray powder diffraction pattern of the crystalline Form I shows characteristic peaks at 2theta values of 22.7°±0.2°, 24.4°±0.2°, 26.3°±0.2°.

4. The crystalline Form I according to claim 1, wherein the X-ray powder diffraction pattern of the crystalline Form I shows one or two or three of the characteristic peaks at 2theta values of 7.8°±0.2°, 15.7°±0.2°, 16.7°±0.2°.

5. The crystalline Form I according to claim 4, wherein the X-ray powder diffraction pattern of the crystalline Form I shows characteristic peaks at 2theta values of 7.8°±0.2°, 15.7°±0.2°, 16.7°±0.2°.

6. The crystalline Form I according to claim 1, wherein said Form I has an X-ray powder diffraction pattern substantially as depicted in FIG. 5.

7. A process for preparing the crystalline Form I according to claim 1, comprising:
dissolving compound I mono-succinate in a mixed solvent of alcohols and one or more solvents selected from the group consisting of alkyl nitriles and alkanes, or dissolving compound I mono-succinate in a mixture of water and one or more solvents selected from the group consisting of alkyl nitriles, to form a mixture; and stirring the mixture until solids precipitate out.

8. The process according to claim 7, wherein said alcohol in mixed solvent is methanol, ethanol or a combination thereof, said alkyl nitrile in mixed solvent is acetonitrile, said alkane in mixed solvent is n-heptane.

9. The process according to claim 8, wherein said mixed solvents are acetonitrile and methanol, ethanol and n-heptane or acetonitrile and water.

10. A pharmaceutical composition comprising a therapeutically effective amount of the mono-succinate Form I according to claim 1 and pharmaceutical acceptable carrier.

* * * * *